US012701313B2

(12) United States Patent
    Kagawa

(10) Patent No.: US 12,701,313 B2
(45) Date of Patent: Aug. 4, 2026

(54) LIGHT SOURCE APPARATUS, IMAGE PICKUP APPARATUS, AND ENDOSCOPE SYSTEM

(71) Applicant: OLYMPUS MEDICAL SYSTEMS CORP., Tokyo (JP)

(72) Inventor: Ryohei Kagawa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 76 days.

(21) Appl. No.: 18/961,784

(22) Filed: Nov. 27, 2024

(65) Prior Publication Data

US 2025/0175691 A1      May 29, 2025

Related U.S. Application Data

(60) Provisional application No. 63/603,859, filed on Nov. 29, 2023.

(51) Int. Cl.
| | |
|---|---|
| *H04N 23/56* | (2023.01) |
| *A61B 1/06* | (2006.01) |
| *A61B 1/267* | (2006.01) |
| *H04N 23/50* | (2023.01) |
| *H05B 47/16* | (2020.01) |

(52) U.S. Cl.
    CPC ........... *H04N 23/56* (2023.01); *A61B 1/0655* (2022.02); *A61B 1/0684* (2013.01); *A61B 1/2673* (2013.01); *H04N 23/555* (2023.01); *H05B 47/16* (2020.01)

(58) Field of Classification Search
    None
    See application file for complete search history.

(56) References Cited

U.S. PATENT DOCUMENTS

| | | |
|---|---|---|
| 2017/0064178 A1 | 3/2017 | Kagawa et al. |
| 2019/0142264 A1* | 5/2019 | Bos ........................ H04N 23/66 600/188 |
| 2019/0142265 A1* | 5/2019 | Bos .................... A61B 1/00006 600/188 |

FOREIGN PATENT DOCUMENTS

| | | | |
|---|---|---|---|
| JP | 2016052453 A | * | 4/2016 |
| JP | 5948512 B2 | | 7/2016 |

* cited by examiner

*Primary Examiner* — Paul M Berardesca
(74) *Attorney, Agent, or Firm* — Scully, Scott, Murphy & Presser, P.C.

(57) ABSTRACT

A light source apparatus includes at least one processor comprising hardware. The at least one processor is configured to determine, in a first unit, a first frequency of a pulsed light with a first resolution and a second frequency of pulsed light with a second resolution based on a vibration frequency of an object, the first resolution being more precise than the second resolution, determine a difference between the first frequency and the second frequency in the first unit, and when the accumulated differences reach a first predetermined value, add a second predetermined value to the first frequency in a second unit subsequent to the first unit, and subtract a third predetermined value from the accumulated differences in the second unit.

15 Claims, 12 Drawing Sheets

LIGHT SOURCE APPARATUS, IMAGE PICKUP APPARATUS, AND ENDOSCOPE SYSTEM

RELATED APPLICATION DATA

This application is based on and claims priority under 35 U.S.C. § 119 to U.S. provisional Application No. 63/603,859, filed on Nov. 29, 2023, the entire contents of which are incorporated herein by reference.

BACKGROUND

Field

The present disclosure relates to a light source apparatus, an image pickup apparatus, and an endoscope system that are suitable for observing a vibrating object.

Description of the Related Art

In recent years, image pickup apparatuses using an image pickup device such as a CMOS sensor and the like have been used in various fields. In medical fields, for example, electronic endoscope apparatuses using an image pickup device are employed in some cases as endoscope apparatuses used for diagnosis, treatment, and the like. Such electronic endoscopes have on a distal end side thereof an elongated insertion portion, and an image pickup device at the distal end of the insertion portion. An image pickup signal acquired by the endoscope is supplied to a video processor, and an endoscopic image is generated in the video processor.

Image pickup apparatuses such as endoscopes or the like pick up an image of an object, with the object illuminated intermittently, to thereby be capable of observing a stopped state or a slow-motion state of an object such as a vocal cord that moves at a high speed. There is a case where a rolling-shutter CMOS sensor is employed as an image pickup device employed in such endoscopes. In the rolling-shutter method, reset, exposure, and readout are performed at different timings for each line. Therefore, in the rolling-shutter method, exposure timing differs for each horizontal line during one image pickup period, which is likely to result in uneven luminance in images.

In view of the above, Japan Patent No. 5948512 (hereinafter, referred to as Patent Literature 1) discloses a processing apparatus that processes a pixel signal of a plurality of pixels that receive light from an object that is illuminated with pulsed light, perform photoelectric conversion on the received light, and generate the pixel signal. The processing apparatus includes a signal processing section that generates, from the pixel signal, an illumination time pixel signal corresponding to the pixel signal in a case where the plurality of pixels are exposed in an illumination period of the pulsed light according to the state of overlapping of the illumination period of the pulsed light and the readout timing of the pixel signal.

SUMMARY

A light source apparatus includes at least one processor comprising hardware. The at least one processor is configured to determine, in a first unit, a first frequency of a pulsed light with a first resolution and a second frequency of pulsed light with a second resolution based on a vibration frequency of an object, the first resolution being more precise than the second resolution, determine a difference between the first frequency and the second frequency in the first unit, and when the accumulated differences reach a first predetermined value, add a second predetermined value to the first frequency in a second unit subsequent to the first unit, and subtract a third predetermined value from the accumulated differences in the second unit.

A light source apparatus according to one aspect of the present disclosure includes at least one processor comprising hardware. The at least one processor is configured to control a light source that generates pulsed light with which an object is illuminated, and cause the light source to generate the pulsed light with a first temporal resolution. The processor is configured to: calculate, based on a vibration frequency of the object, a light emission cycle of the pulsed light with a second temporal resolution which is more precise than the first temporal resolution; round the light emission cycle calculated with the second temporal resolution to a precision of the first temporal resolution, to set the light emission cycle obtained by the rounding as the light emission cycle of the pulsed light that is generated by the light source; accumulate an error between the light emission cycle calculated with the second temporal resolution and the light emission cycle with the first temporal resolution that is calculated by the rounding; increase the light emission cycle with the first temporal resolution in a unit of the first temporal resolution and decrease the accumulated error in the unit of the first temporal resolution, when the accumulated error reaches a predetermined positive value; and decrease the light emission cycle with the first temporal resolution in the unit of the first temporal resolution and increase the accumulated error in the unit of the first temporal resolution, when the accumulated error reaches a predetermined negative value.

DETAILED DESCRIPTION

Hereinafter embodiments of the present disclosure are described in detail with reference to drawings.

First Embodiment

Figure 1:
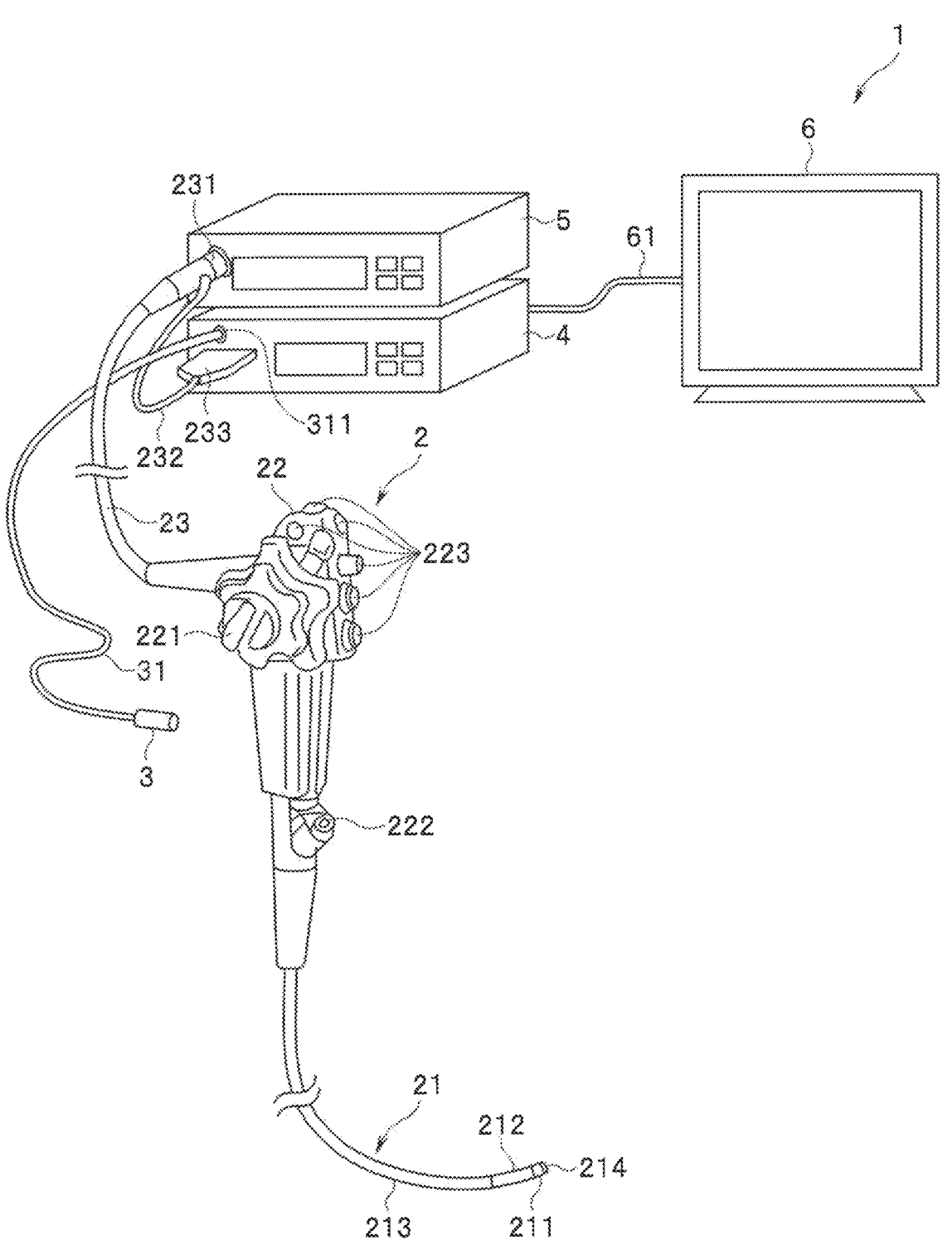
FIG. 1 is a block diagram showing an endoscope system including a light source apparatus according to a first embodiment of the present disclosure.
Figure 2:
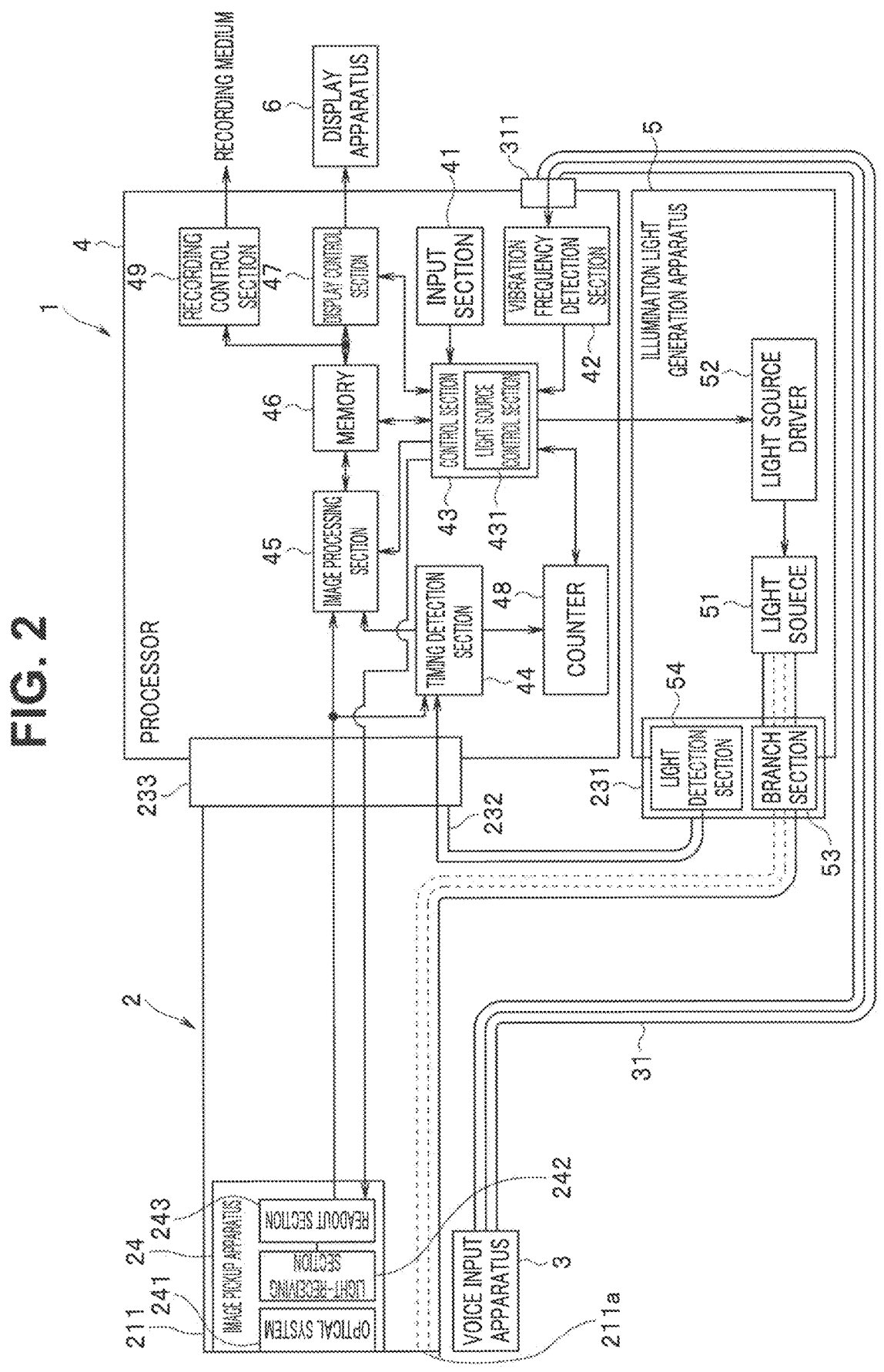
FIG. 2 is a block diagram showing an example of a specific configuration of the endoscope system in FIG. 1.

FIG. 1 is a block diagram showing an endoscope system including a light source apparatus according to a first embodiment of the present disclosure. FIG. 2 is a block diagram showing an example of a specific configuration of the endoscope system in FIG. 1. The present embodiment eliminates variation in brightness in adjacent frames to improve an image quality, by obtaining an image signal with an arithmetic operation according to an overlapping state between an illumination timing of pulsed light and a readout timing of a pixel signal. The present embodiment enables, such as, a smooth slow-motion observation.

Note that the present embodiment will be described by taking an endoscope configured to observe a vocal cord as an object that moves at a high speed, as an example. However, an image pickup object is not limited to a vocal cord, but the present embodiment can be applied to various image pickup apparatuses that pick up images of various objects that move at a high speed.

An endoscope system 1 shown in FIG. 1 includes an endoscope 2, a voice input apparatus 3, a processor 4 (at least one processor), an illumination light generation apparatus 5, and a display apparatus 6. Note that the illumination light generation apparatus 5 and a part of the processor 4 constitute a light source apparatus. In addition, the light source apparatus, an image pickup apparatus provided in the endoscope 2, and a part of the processor 4 constitute an image pickup apparatus.

The endoscope 2 includes an insertion portion 21 that is long and has flexibility, and is configured to be inserted into a body cavity of a subject, and an operation portion 22 connected to a proximal end of the insertion portion 21 and including various operating devices. The insertion portion 21 incorporates an illumination fiber (light guide cable), an electric cable, and the like. The insertion portion 21 includes a distal end portion 211 including an image pickup apparatus that incorporates a CMOS image pickup device as an image pickup device that picks up an image inside a subject, a bendable bending portion 212 constituted of a plurality of bending pieces, and a flexible tube portion 213 having flexibility and provided on the proximal end portion side of the bending portion 212. On a distal end surface 214 of the distal end portion 211, an illumination lens for irradiating the subject with illumination light, an opening portion with which a treatment instrument channel is communicated, and a distal end of an air/water feeding nozzle (not shown) are disposed.

The operation portion 22 is provided with a bending knob 221, a treatment instrument insertion portion 222, and a switch section 223. The bending portion 212 can be bent in the up-down direction and the left-right direction by operating the bending knob 221. The switch section 223 includes a plurality of switches for operating the processor 4, the illumination light generation apparatus 5, and peripheral apparatuses such as an air feeding apparatus, a water feeding apparatus, a gas feeding apparatus, etc. Treatment instruments such as a biological forceps, a laser knife, etc., are inserted into the treatment instrument insertion portion 222.

The treatment instrument inserted from the treatment instrument insertion portion 222 passes through the treatment instrument channel provided inside the insertion portion 21, to be protruded from the distal end surface 214 at the distal end of the insertion portion 21.

A universal cord 23 is extended from the operation portion 22, and the endoscope 2 is connected to the processor 4 and the illumination light generation apparatus 5 through a connector 231 provided at an end portion of the universal cord 23. The universal cord 23 is configured by using an illumination fiber, an electric cable, and the like. The connector 231 is detachably connected to the illumination light generation apparatus 5, branches to a branching cord 232, and is detachably connected to the processor 4 through a connector 233 provided at an end portion of the branching cord 232. The universal cord 23 transmits an image pickup signal obtained by image pickup by the image pickup apparatus provided in the distal end portion 211 to the processor 4 through the connector 233. The universal cord 23 supplies the illumination light emitted from the illumination light generation apparatus 5 to the endoscope 2 via the connector 233.

Furthermore, the illumination light supplied to the endoscope 2 is guided to the distal end surface 214 of the distal end portion 211 via the illumination fiber in the insertion portion 21, to be emitted from the distal end surface 214. The illumination light emitted from the distal end surface 214 toward the subject is reflected by the subject, and guided to the image pickup surface (light-receiving section) of the image pickup apparatus via an observation window provided on the distal end surface 214, to be image-formed on the image pickup surface. The image pickup apparatus photo-electrically converts an optical image formed on the image pickup surface to obtain an image pickup signal. The image pickup signal is supplied to the processor 4 via the cable in the insertion portion 21 and the universal cord 23.

The voice input apparatus 3 is configured to acquire voice. When an observation of the vocal cord is performed, for example, the voice input apparatus 3 is arranged at a position where the voice emitted from the vocal cord is received. The voice input apparatus 3 is connected to a cord 31, and a connector 311 located on the proximal end side of the cord 31 is detachably connected to the processor 4. The voice input apparatus 3 outputs a voice signal based on the acquired voice to the processor 4 through the cord 31. The voice input apparatus 3 can be a microphone, or acoustic sensor.

The processor 4 receives an image pickup signal of the inside of the subject, which has been obtained by picking up an image of the inside of the subject by the image pickup apparatus of the endoscope 2, through the universal cord 23, and performs predetermined image processing on the received image pickup signal. The processor 4 receives also various operation signals from the switch section 223, through the universal cord 23, and controls the respective sections in the endoscope system 1, based on the received operation signals.

The illumination light generation apparatus 5 is configured by a light source configured to emit pulsed white light, a light condensing lens, and the like. The illumination light generation apparatus 5 emits the pulsed white light (pulsed light) from the white light source to the endoscope 2 as illumination light. The pulsed light is, as described above, applied to the object from the distal end surface 214 of the distal end portion 211 through the universal cord 23 and the illumination fiber incorporated in the insertion portion 21. Note that the pulsed light emitted from the illumination light generation apparatus 5 is partially branched and converted into a pulse signal in the connector 231, and thereafter supplied to the processor 4 through the branching cord 232 and the connector 233.

The display apparatus 6 is configured of a display using a liquid crystal, an organic EL (electroluminescence), or the like. The display apparatus 6 receives the image subjected to the predetermined image processing by the processor 4 through a video cable 61, and displays various kinds of information based on the received image. This enables an operator to arrange the distal end portion 211 of the endoscope 2 at a desired position, while watching the image (observation image inside the body) displayed on the display apparatus 6, to observe a desired position inside a desired subject.

(Illumination Time Pixel Signal)

Figure 3:
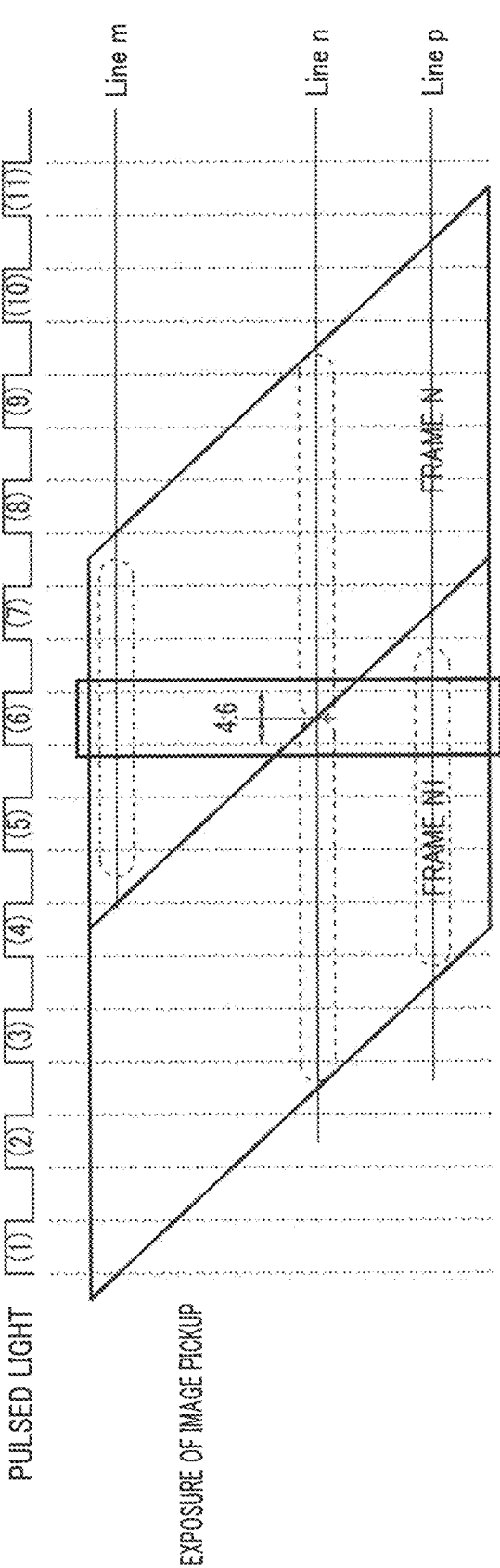
FIG. 3 is an explanatory view describing an arithmetic operation for obtaining an illumination time pixel signal in the Patent Literature 1.

FIG. 3 is an explanatory view for describing an arithmetic operation for obtaining an illumination time pixel signal in the Patent Literature 1. FIG. 3 shows the time period on the horizontal axis, with the upper row (pulsed light) showing a generation timing of pulsed light for intermittent illumination of the object, and the lower row (exposure for image pickup) showing the exposure and readout timing. The vertical axis on the lower row in FIG. 3 shows respective lines in the vertical direction of the image pickup device.

In the rolling-shutter method, the image pickup device that configures the image pickup apparatus changes the exposure timing and the readout timing for each horizontal line. Therefore, even for the pixel signals of the same frame, the exposure period and readout timing vary for each horizontal line. Each parallelogram frame in FIG. 3 shows each frame. In one parallelogram frame, the temporally preceding oblique line part shows the exposure start timing of each frame, and the temporally succeeding oblique line part shows the exposure end timing and the readout timing. FIG. 3 shows that illumination with pulsed light is performed for a plurality of times in one frame period, and for the frame N, for example, illumination is performed with a part of fourth pulsed light (4), fifth pulsed light (5) to tenth pulsed light (10), and a part of eleventh pulsed light (11). Note that, in the endoscope, the object is illuminated in a period in which pulsed light is generated, and therefore, the image pickup device is exposed in the period in which the object is illuminated with the pulsed light within the period in which exposure is performed.

Thus, when the rolling-shutter method is employed, the exposure period temporally shifts for each horizontal line even in the same frame. Therefore, if the light emission cycle of the pulsed light does not coincide with the frame period of the image pickup device, the image pickup device is exposed in the single pulsed light illumination over a plurality of frames in some cases. As a result, even for the same horizontal line, the number of times of illumination and illumination period differ from one frame to another, resulting in variations in brightness for each horizontal line from one frame to another.

For example, for the horizontal line (Line) m in the frame N, exposure is performed with the fifth pulsed light (5) to the seventh pulsed light (7), while, for the horizontal line p in the frame N−1, exposure is performed with the fourth pulsed light (4) to the sixth pulsed light (6) and a part of the seventh pulsed light (7). In addition, for the horizontal line n in the frame N, exposure is performed with the seventh pulsed light (7) to the ninth pulsed light (9), and the exposure is performed in the latter ⅗ period of the sixth pulsed light (6). In addition, for the horizontal line n in the frame N−1, exposure is performed with the third pulsed light (3) to the fifth pulsed light (5), and the exposure is performed in the former ⅖ period of the sixth pulsed light (6).

In view of the above, in Patent Literature 1, an arithmetic operation is performed, in which one pulsed light in one frame is selected as a selected pulse, and for each horizontal line, synthesizing processing (hereinafter referred to as a synthesizing arithmetic operation) is performed according to a ratio (synthesizing ratio) between an exposure amount by all pulses (all-pulse exposure amount) and an exposure amount by the selected pulse (selected-pulse exposure amount). With such an arithmetic operation, the pixel signal (illumination time pixel signal), which is similar to the pixel signal in the case where exposure is evenly performed in all the horizontal lines, is obtained regardless of the change in the exposure amount (exposure time period).

For example, assume that the sixth pulsed light (6) shown by the rectangular bold frame in FIG. 3 is selected as the selected pulsed light. Note that it is assumed that the light amount and the pulse width (light emission period) of each pulsed light are the same. An illumination time pixel signal that is common to two frames, i.e., the frame N−1 and the frame N, is obtained. For example, for the horizontal line m, exposure by the selected pulse (6) is performed only in the frame N, and the illumination time pixel signal is obtained by multiplying the pixel signal read in the frame N by ⅓ which is a ratio between the selected-pulse exposure amount and the all-pulse exposure amount (synthesizing ratio) in the frame N.

On the other hand, for the horizontal line n, the exposure by the selected pulse (6) is performed both in the frame N−1 and the frame N. Then, the illumination time pixel signal is obtained by calculating a sum of a result obtained by multiplying the pixel signal read in the frame N−1 by 0.4/3.4 which is a synthesizing ratio in the frame N−1 and a result obtained by multiplying the pixel signal read in the frame N by 0.6/3.6 which is a synthesizing ratio in the frame N.

Thus, in the Patent Literature 1, it is possible to obtain the illumination time pixel signal, which is the same as the one in the case where exposure is evenly performed for all the horizontal lines in all of the frames, and prevent variation in brightness in each horizontal line from frame to frame.

(Optical Pulse Temporal Resolution)

The illumination light generation apparatus 5 that generates pulsed light is configured to be capable of changing light emission timing. Although the oblique line indicating the start of exposure period is shown as a linear line in FIG. 3, the start timing of exposure is shifted by 1 horizontal line period (single horizontal line period) between a predetermined line and the next line. If the light emission timing of the pulsed light shifts from the start timing and end timing of 1 horizontal line period, when the synthesizing ratio is calculated, the number of digits after the decimal point of the numerator and the denominator indicating the synthesizing ratio becomes large, the arithmetic operation amount of the synthesizing arithmetic operation for obtaining the illumination time pixel signal remarkably increases.

In view of the above, a method is employed in which the rising timing and falling timing of the pulsed light are made to coincide with the start timing and the end timing of 1 horizontal line period, to thereby obtain the illumination time pixel signal and reduce the arithmetic operation amount of the synthesizing arithmetic operation. This means that the temporal resolution of the optical pulse is limited to the 1 horizontal line period. In other words, the cycle of the pulsed light is limited to an interval based on the 1 horizontal line period, and as a result, the frequency of the pulsed light is limited.

Now it is assumed that slow-motion observation of a vocal cord is performed by picking up an image of the vocal cord by the image pickup device, while illuminating the vocal cord with the pulsed light. The pulsed light is generated at a frequency close to a vocal cord vibration frequency, to thereby enable a slow-motion observation of the vocal cord at a frequency (slow-motion frequency) according to the difference between the vocal cord vibration frequency and the pulsed light frequency. For example, it is supposed that the frequency of the vocal cord is 1000 Hz, and the slow-motion frequency at which smooth observation is possible is 0.5 Hz. In this case, the difference of the cycles based on the difference between the vocal cord vibration frequency and the pulsed light frequency is represented by the following equation (1).

$$1/(1000 \text{ Hz} - 0.5 \text{ Hz}) - 1/1000 \text{ Hz} = 500 \text{ ns} \qquad (1)$$

Meanwhile, the 1 horizontal line period, which is the temporal resolution of the optical pulse, is represented by the equation of $1/(60 \text{ fps} \times 1000 \text{ lines}) = 16$ μs where the vertical resolution of the image pickup device is 1000 lines and the frame rate is 60 Hz, for example. In other words, in order to enable smooth slow-motion observation, the cycle of the pulsed light is required to be controlled with the temporal resolution of 500 ns cycle, for example. However, the precision of the temporal resolution (16 μs) of the pulsed light is extremely coarse, and high precision slow-motion observation cannot be performed. Thus, if the temporal resolution of the pulsed light is limited to the 1 horizontal line period to reduce the amount of the arithmetic operation, smooth movement of the observation image cannot be obtained, which results in a difficulty in the observation of the object.

(Specific Configuration)

In view of the above, in the present embodiment, by taking advantage of the fact that the human dynamic visual acuity is sufficiently low compared to the pulsed light frequency, a cumulative value of cycle differences based on the difference between the pulsed light frequency for obtaining an ideal slow-motion frequency and the frequency of the object is controlled to be maintained within a certain range, to thereby enable a smooth slow-motion observation for the eyes of human beings.

As shown in FIG. 2, the endoscope 2 includes, at the distal end portion 211, the image pickup apparatus 24. The image pickup apparatus 24 includes a light-receiving section 242 (image sensor) configured to generate pixel signals denoting an inside of the subject, based on the optical image formed on the image pickup surface, an optical system 241 such as an objective lens arranged on the image pickup surface side of the light-receiving section 242, and a readout section 243. The image sensor can be a CCD, a CMOS. The first unit can be a period of a horizontal line of an image sensor 242, an image having a plurality of a horizontal lines including pixels, the horizontal line is obtained under the pulsed light for a plurality of times.

The object is illuminated with the pulsed light from the illumination light generation apparatus 5, and the reflected light from the object is received at the light-receiving section 242 that constitutes the image pickup apparatus 24. The light-receiving section 242 includes a plurality of pixels that photoelectrically convert the received light to generate pixel signals. On the light-receiving section 242, a plurality of pixels are arranged in matrix. The light-receiving section 242 includes a plurality of pixel rows (horizontal lines) each including two or more pixels arranged along the horizontal direction, and the plurality of pixel rows are arranged so as to align in the vertical direction. The light-receiving section 242 generates the pixel signals denoting the inside of the subject, based on the optical image formed on the image pickup surface.

The readout section 243 performs exposure of the plurality of pixels on the light-receiving section 242 and readout of the pixel signals from the plurality of pixels. The light-receiving section 242 and the readout section 243 are configured by a CMOS image pickup device, for example, and capable of performing exposure and readout for each horizontal line. The readout section 243 generates pixel signals by the rolling-shutter method in which image pickup operation of exposure and readout is executed starting from the leading horizontal line, and charge reset, exposure, and readout are performed by shifting the timing by 1 horizontal line period for each horizontal line.

Thus, in the image pickup apparatus 24, even in one image pickup period (frame), the exposure timing and the readout timing are different for each horizontal line. The readout section 243 outputs the pixel signals read out from the plurality of pixels on the light-receiving section 242 to the processor 4 through a cable (not shown) and the connector 233. Note that the vertical synchronization signal and the horizontal synchronization signal to be added to the pixel signal outputted from the CMOS image pickup device are inputted also to a timing detection section 44 to be described later.

The illumination light generation apparatus 5 includes a light source 51 and a light source driver 52.

The light source 51 is constituted of a light source such as a white LED that generates pulsed white light and an optical system such as a light condensing lens. The light source 51 generates pulsed light as illumination light to be supplied to the endoscope 2.

The light source driver 52 is controlled by a light source control section 431 to be described later, to supply predetermined power to the light source 51. Then, the pulsed light emitted from the light source 51 is applied from an illumination window 211a of the distal end portion 211 of the insertion portion 21 to the object, via the connector 231 and the universal cord 23 (see FIG. 1). Note that the image pickup apparatus 24 is arranged in the vicinity of the illumination window 211a. The reflection light of the pulsed light, which is from the illumination window 221a, is received by the light-receiving section 242 of the image pickup apparatus 24, as described above.

The connector 231 includes a branch section 53 and a light detection section 54. The branch section 53 is configured of an optical system such as a prism, and branches a part of the pulsed light emitted from the light source 51 to make it to be incident on the light detection section 54. The light detection section 54 converts the pulsed light incident from the branch section 53 into a pulse signal. The light detection section 54 applies the converted pulse signal to the timing detection section 44 of the processor 4, through the branching cord 232 and the connector 233.

The processor 4 includes: an input section 41; a vibration frequency detection section 42; a control section 43; a timing detection section 44; an image processing section 45 (signal processing section); a memory 46; a display control section 47; a counter 48; and a recording control section 49. The respective sections of the processor 4 may be configured by a processor using a CPU (Central Processing Unit), FPGA (Field Programmable Gate Array) and the like, and may operate according to a program stored in a memory, not shown, to control respective sections, or may implement a part of or all of the functions of the respective sections by an electronic circuit of hardware.

The input section 41 is implemented by using operation devices such as a mouse, a keyboard, a touch panel, and the like, and receives input of various kinds of instruction information of the endoscope system 1. Specifically, the input section 41 receives input of subject information (for example, ID, date of birth, name, etc.), identification information of the endoscope 2 (for example, ID and examination items), and various kinds of instruction information such as examination contents.

The vibration frequency detection section 42 detects a frequency of the voice inputted to the voice input apparatus 3, and then inputted to the processor 4 through the cord 31 and the connector 311. For example, in the case where the vocal cord is observed by the endoscope 2, the voice inputted through the connector 311 is uttered from the vocal cord as the object. The vibration frequency detection section 42 outputs the detected frequency of the voice to the control section 43.

The timing detection section 44 detects, based on the pulse signal from the light detection section 54, an illumination timing and an illumination period of the pulsed light generated by the illumination light generation apparatus 5. The timing detection section 44 detects, based on the vertical synchronization signal and the horizontal synchronization signal to be added to the pixel signal outputted from the image pickup apparatus 24, the readout timing of the pixel signal by the readout section 243 for each of the horizontal lines. The timing detection section 44 acquires the readout timing, the illumination timing, and the illumination period, and detects, from the pixel signals read out by the readout section 243, the horizontal line in which the readout timing of the pixel signal overlaps the illumination period of the selected pulse, as an overlap line. In the example shown in FIG. 3, for example, the overlap line is a horizontal line in which the oblique line indicating the readout timing overlaps the illumination period of the selected pulse (6).

The image processing section 45 performs predetermined signal processing on the pixel signals of the plurality of pixels read by the readout section 243 of the image pickup apparatus 24. For example, the image processing section 45 performs, on the pixel signals, image processing including at least optical black subtraction processing, white balance (WB) adjustment processing, image signal synchronization processing if the image pickup device is a Bayer array, color matrix arithmetic operation processing, gamma correction processing, color reproduction processing, and edge enhancement processing, etc.

The image processing section 45 determines, from the pixel signals of the plurality of pixels read by the readout section 243 of the image pickup apparatus 24, the overlap line and lines other than the overlap line, depending on an overlapping state where the illumination timing and illumination period of the pulsed light by the illumination light generation apparatus 5 overlap the readout timing of the pixel signals by the readout section 243, and generates illumination time pixel signals as the pixel signals in the case where a plurality of pixels are exposed in the illumination period of the pulsed light by the illumination light generation apparatus 5. In other words, the image processing section 45 performs the above-described synthesizing arithmetic operation, to generate the illumination time pixel signals from the pixel signals of a plurality of consecutive frames stored in the memory 46 to be described later.

The memory 46 is implemented by using a volatile memory or a non-volatile memory, and stores various kinds of programs for causing the processor 4 and the illumination light generation apparatus 5 to operate. The memory 46 temporarily records the information which is being processed in the processor 4. The memory 46 stores the pixel signals read out by the readout section 243 in frame units, corresponding to the matrix arrangement of the plurality of pixels in the light-receiving section 242. The memory 46 stores the illumination time pixel signals generated by the image processing section 45 in frame units. The memory 46 may be configured by a memory card or the like that is mounted from the outside of the processor 4. In addition, the memory 46 also stores the accumulated error calculated in the light emission control by the light source control section 431, which is described below.

The display control section 47 generates, in accordance with the display cycle of the display apparatus 6, data for display to be displayed on the display apparatus 6, from the illumination time pixel signals of the plurality of frames, which have been generated by the image processing section 45. The display control section 47 selects, for each display cycle of the display apparatus 6, data for display among the illumination time pixel signals of the plurality of frames, which have been generated by the image processing section 45. Alternatively, the display control section 47 synthesizes the illumination time pixel signals of the plurality of frames, which have been generated by the image processing section 45 for each display cycle of the display apparatus 6, to generate the data for display. The display control section 47 converts the data for display from a digital signal to an analog signal, and changes the image data of the converted analog signal to a format such as high-definition system, to output the image data to the display apparatus 6.

The recording control section 49 receives the image processed by the image processing section 45 and the voice taken by the voice input apparatus 3, (illustration omitted), encodes the image and the voice in a predetermined format, and records the encoded image and voice in the recording medium.

(Pulsed Light Generation Control)

The exposure amount of the image pickup apparatus 24 changes depending on the irradiation time period of the pulsed light, that is, the pulse width (pulse cycle) of the pulsed light. The light source control section 431 of the control section 43 controls the light source driver 52, to perform pulse width control (PWM: pulse width modulation) of the pulsed light emitted from the light source 51. As described above, the cycle of the pulsed light emitted from the illumination light generation apparatus 5 (hereinafter, referred to as an actual light emission cycle) is controlled with the temporal resolution in 1 horizontal line period.

In the present embodiment, the light source control section 431 controls the actual light emission cycle of the pulsed light emitted from the illumination light generation apparatus 5 is controlled with the temporal resolution in the 1 horizontal line period, while the ideal light emission cycle of the pulsed light, which is calculated by the arithmetic operation (hereinafter, referred to as the ideal light emission cycle) is calculated with the precision of a decimal horizontal line period shorter than 1 horizontal line period. Then, the light source control section 431 causes the memory 46 or a memory not shown to store an accumulated error of the difference between the ideal light emission cycle and the actual light emission cycle, and changes the actual light emission cycle in the 1 horizontal line period unit such that the accumulated error falls within a predetermined range, to thereby enable the high precision slow-motion observation. Note that the ideal light emission cycle indicates the light emission cycle of the pulsed light that enables the high precision slow-motion observation. Note that considering that the actual light emission cycle is in 1 horizontal line period unit, the predetermined range of, for example, ±0.5 horizontal line cycle can be used, but is not limited to any particular range.

For example, when the slow-motion observation of the vocal cord is performed, the vibration frequency detection section 42 obtains the vibration frequency of the vocal cord vibration, that is, the frequency of the voice generated with the vocal cord vibration (vocal cord vibration frequency). When the optimum pulsed light frequency for the slow-motion observation calculated on the basis of the vocal cord vibration frequency is Pf, the ideal number of light-emitting lines Pinl, which represents the ideal light emission cycle in the horizontal line period unit, is given by the following equation (2).

$$Pinl = 1 \text{ horizontal line frequency}/Pf \qquad (2)$$

The light source control section 431 calculates the pulsed light frequency Pf based on the vocal cord vibration frequency obtained by the vibration frequency detection section 42, and calculates the ideal number of light-emitting lines Pinl, based on the equation (2). The light source control section 431 calculates the ideal number of light-emitting lines Pinl in the equation (2) up to the decimal precision that enables sufficiently high precision slow-motion observation.

In addition, the light source control section 431 sets, as the actual light emission cycle, the horizontal line period obtained by rounding off the digits after the decimal point of the ideal number of light-emitting lines Pinl, for example. For example, the ideal number of light-emitting lines Pinl is calculated as 125.35 horizontal line period, the light source control section 431 uses the output of the counter 48 to set the actual number of light-emitting lines Prnl representing the actual light emission cycles in the unit of horizontal line period to 125 horizontal line period. Note that the actual number of light-emitting lines Prnl may be an integer value in the horizontal line period unit corresponding to the ideal number of light-emitting lines Pinl, and not only rounding off the digits after the decimal point of the ideal number of light-emitting lines Pinl but also rounding up or rounding down to the nearest decimal may be performed.

The counter 48 counts the horizontal synchronization signals received from the timing detection section 44. The light source control section 431 uses the output of the counter 48 to set the actual light emission cycle to the light source driver 52. The light source control section 431 successively calculates the actual number of light-emitting lines Prnl while updating the ideal number of light-emitting lines Pinl by repeating the arithmetic operation of the above-described equation (2) at a predetermined cycle, to set the actual light emission cycle, and calculates a cumulative value (accumulated error) of the error between the actual number of light-emitting lines Prnl and the ideal number of light-emitting lines Pinl. When the accumulated error reaches a predetermined value, the light source control section 431 increases or decreases the actual number of light-emitting lines Prnl in the 1 horizontal line period unit to correct the actual number of light-emitting lines, to reduce the accumulated error.

In other words, the light source apparatus according to the present embodiment is configured of: the control section 43 that includes the light source control section 431; the vibration frequency detection section 42; the counter 48; the illumination light generation apparatus 5, etc., and the light source control section 431 changes the actual light emission cycle such that the accumulated error falls within a predetermined range. The pulsed light frequency corresponding to the vocal cord vibration frequency is sufficiently higher than the dynamic visual acuity of the human eyes, and it can be supposed that an average value of the accumulated errors over a predetermined period affects the visual recognition of human eyes. When the accumulated errors in the period during which a plurality of pulsed lights are generated are averaged, the accumulated error per one pulsed light is sufficiently small, to be equivalent to setting the actual light emission cycle with the precision which is the same as the precision in the case where the actual number of light-emitting lines Prnl is set with the decimal precision. Thus, smooth slow-motion observation is possible in the present embodiment.

(Operation)

Figure 4:
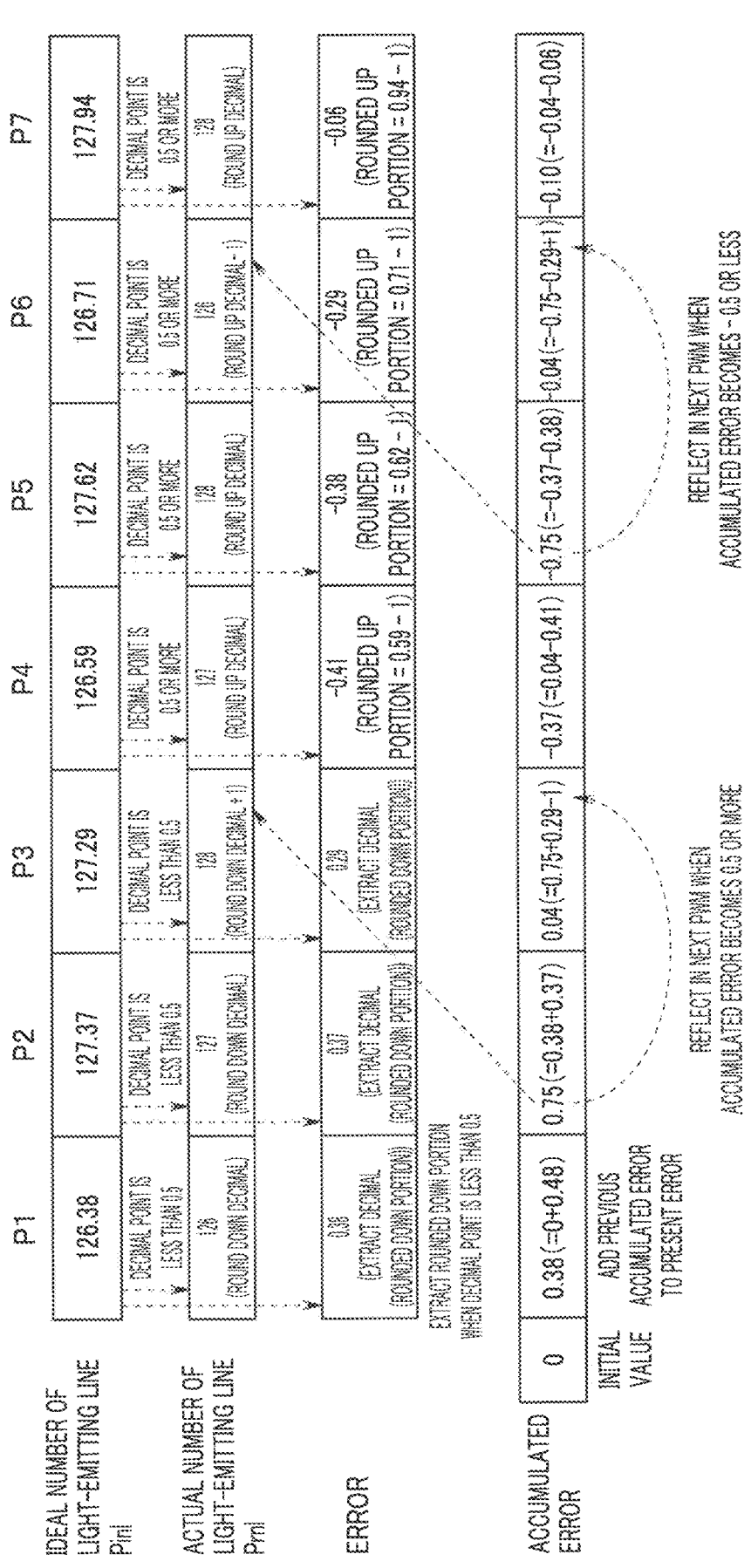
FIG. 4 is an explanatory view showing an ideal number of light-emitting lines Pinl, an actual number of light-emitting lines Prnl, errors, and accumulated errors for successive pulsed light P1, P2, . . . , P7.

Next, the operation of the embodiment thus configured will be described with reference to FIG. 4. FIG. 4 is an explanatory view showing the ideal number of light-emitting lines Pinl, the actual number of light-emitting lines Prnl, the errors, and the accumulated errors for successive pulsed lights P1, P2, . . . , P7.

The light source control section 431 calculates the ideal number of light-emitting lines Pinl with the predetermined decimal precision, based on the equation (2). In the example in FIG. 4, for the pulsed light P1, the ideal number of light-emitting lines Pinl is 126.38 horizontal line period. The light source control section 431 rounds off the digits after the decimal point of the ideal number of light-emitting lines, for example, to set the actual number of light-emitting lines Prnl. In this case, the value after the decimal point of the ideal number of light-emitting lines Pinl is 0.38, and the actual number of light-emitting lines Prnl is calculated as 126 horizontal line period by rounding off the digits after the decimal point. The light source control section 431 uses the output of the counter 48 to control the light source driver 52 to generate the pulsed light P1, the pulse width of which is 126 horizontal line period width, from the start of the horizontal line period, for example.

In addition, the light source control section 431 calculates an error generated by the rounding processing for calculating the actual number of light-emitting lines Prnl, that is, the difference of 0.38 between the ideal number of light-emitting lines Pinl and the actual number of light-emitting lines Prnl and obtain the accumulated error. The initial value of the accumulated error is 0, and 0.38 horizontal line period is stored in the memory 46 as the accumulated error. When the 126 horizontal line period elapses from the falling of the pulsed light P1, the next pulsed light P2 is emitted.

In the case of the vocal cord observation, since the vocal cord vibration frequency successively changes, the light source control section 431 executes the arithmetic operation of the above-described equation (2) at each predetermined period, to calculate the ideal number of light-emitting lines Pinl. In the example shown in FIG. 4, at the light emission timing of the pulsed light P2, 127.37 horizontal line period is obtained as the ideal number of light-emitting lines Pinl. The light source control section 431 obtains 127 horizontal line period as the actual number of light-emitting lines Prnl by rounding off the digits after the decimal point, for example. The light source control section 431 uses the output of the counter 48, to control the light source driver 52 so as to generate the pulsed light P2, the pulse width of which is 127 horizontal line period width.

In addition, the light source control section 431 calculates the difference of 0.37 between the ideal number of light-emitting lines Pinl and the actual number of light-emitting lines Prnl and obtains 0.75 (=0.38+0.37) horizontal line period as the accumulated error, to update the accumulated error in the memory. When the 127 horizontal line period elapses from the falling of the pulsed light P2, the next pulsed light P3 is emitted.

In the example shown in FIG. 4, at the light emission timing of the pulsed light P3, 127.29 horizontal line period is obtained as the ideal number of light-emitting lines Pinl. The light source control section 431 obtains 127 horizontal line period by rounding off the digits after the decimal point of the ideal number of light-emitting lines Pinl, for example. The light source control section 431 monitors whether the accumulated error stored in the memory exceeds the predetermined range. In the example shown in FIG. 4, for example, 0.5 is employed as the predetermined range. Since the accumulated error stored in the memory exceeds the predetermined range at the time point of the emission of the pulsed light P3, the light source control section 431 increases or decreases the actual number of light-emitting lines Prnl in the 1 horizontal line period unit to correct the actual number of light-emitting lines, according to the error value exceeding the predetermined range. In this case, the light source control section 431 sets, for the pulsed light P3, 128 (=127+1) horizontal line period as the actual number of light-emitting lines Prnl after the correction. The light source control section 431 uses the output of the counter 48, to control the light source driver 52 so as to generate the pulsed light P3, the pulse width of which is 128 horizontal line period width.

In addition, the light source control section 431 calculates the difference of 0.29 between the ideal number of light-emitting lines Pinl and the pre-correction actual number of light-emitting lines Prn, and obtains 0.04 (=0.75+0.29−1) horizontal line period as the accumulated error, to update the accumulated error stored in the memory. When the 128 horizontal line period elapses from the falling of the pulsed light P3, the next pulsed light P4 is emitted.

In the example shown in FIG. 4, at the light emission timing of the pulsed light P4, 126.59 horizontal line period is obtained as the ideal number of light-emitting lines Pinl. In this case, since the accumulated error stored in the memory does not exceed the predetermined range, the light source control section 431 rounds off the digits after the decimal point of the ideal number of light-emitting line Pinl, for example, to obtain 127 horizontal line period as the actual number of light-emitting lines Prnl. The light source control section 431 uses the output of the counter 48, to control the light source driver 52 so as to generate the pulsed light P4, the pulse width of which is 127 horizontal line period width.

In addition, the light source control section 431 calculates the difference of −0.41 between the ideal number of light-emitting lines Pinl and the actual number of light-emitting lines Prnl and obtains −0.37 (=0.04−0.41) horizontal line period as the accumulated error, to update the accumulated error stored in the memory. When the 127 horizontal line period elapses from the falling of the pulsed light P4, the next pulsed light P5 is emitted.

In the example shown in FIG. 4, at the light emission timing of the pulsed light P5, 127. 62 horizontal line period is obtained as the ideal number of light-emitting lines Pinl.

In this case, since the accumulated error stored in the memory does not exceed the predetermined range, the light source control section 431 rounds off the digits after the decimal point of the ideal number of light-emitting line Pinl, for example, to obtain 128 horizontal line period as the actual number of light-emitting lines Prnl. The light source control section 431 uses the output of the counter 48, to control the light source driver 52 so as to generate the pulsed light P5, the pulse width of which is 128 horizontal line period width.

In addition, the light source control section 431 calculates the difference of −0.38 between the ideal number of light-emitting lines Pinl and the actual number of light-emitting lines Prnl and obtains −0.75 (=−0.37−0.38) horizontal line period as the accumulated error, to update the accumulated error stored in the memory. When the 128 horizontal line period elapses from the falling of the pulsed light P5, the next pulsed light P6 is emitted.

In the example shown in FIG. 4, at the light emission timing of the pulsed light P6, 126. 71 horizontal line period is obtained as the ideal number of light-emitting lines Pinl. In this case, since the accumulated error stored in the memory exceeds the predetermined range, the light source control section 431 obtains the post-corrected actual number of light-emitting lines Prnl (126) by subtracting 1 from the actual number of light-emitting line Prnl (127) obtained by rounding off the digits after the decimal point, for example, of the ideal number of light-emitting lines Pinl. The light source control section 431 uses the output of the counter 48, to control the light source driver 52 so as to generate the pulsed light P6, the pulse width of which is 126 horizontal line period width.

In addition, the light source control section 431 calculates the difference of −0.29 between the ideal number of light-emitting lines Pinl and the pre-correction actual number of light-emitting lines Prnl, and obtains −0.04 (=−0.75−0.29+1) horizontal line period as the accumulated error, to update the accumulated error in the memory. When the 126 horizontal line period elapses from the falling of the pulsed light P6, the next pulsed light P7 is emitted.

In the example shown in FIG. 4, at the light emission timing of the pulsed light P7, 127. 94 horizontal line period is obtained as the ideal number of light-emitting lines Pinl. In this case, since the accumulated error stored in the memory does not exceed the predetermined range, the light source control section 431 rounds off the digits after the decimal point of the ideal number of light-emitting line Pinl, for example, to obtain 128 horizontal line period as the actual number of light-emitting lines Prnl. The light source control section 431 uses the output of the counter 48, to control the light source driver 52 so as to generate the pulsed light P7, the pulse width of which is 128 horizontal line period width.

In addition, the light source control section 431 calculates the difference of −0.06 between the ideal number of light-emitting lines Pinl and the actual number of light-emitting lines Prnl, and obtains −0.10 (=−0.04−0.06) horizontal line period as the accumulated error, to update the accumulated error stored in the memory. When the 128 horizontal line period elapses from the falling of the pulsed light P7, the next pulsed light is emitted.

After that, the same operation is repeated to correct the actual number of light-emitting lines Prnl such that a cumulative value (accumulated error) of the difference between the actual number of light-emitting lines Prnl and the ideal number of light-emitting lines Pinl falls within the predetermined range. Thus, according to the present embodiment, the accumulated error is a value that constantly falls within the predetermined range, and the accumulated error does not increase to the extent that observation is possible with the human eyes. In other words, the precision for each one pulsed light cannot meet the precision required for slow-motion observation, but an average precision of a plurality of pulsed lights can achieve a sufficient precision. Considering the human dynamic visual acuity, it can be assumed that people interpret the average error of each of a plurality of pulsed lights rather than the error of each pulsed light, and can be regarded that the required precision of the slow-motion observation is achieved in the present embodiment. Thus, the present embodiment enables smooth slow-motion observation with the human eyes.

The at least one processor 4 comprises hardware. The at least one processor 4 can be configured to determine, in a first unit, a first frequency of a pulsed light with a first resolution and a second frequency of pulsed light with a second resolution based on the vibration frequency of the object, the first resolution is more precise than the second resolution. The at least one processor 4 can be configured to determine a difference between the first frequency and the second frequency in the first unit, determine accumulated differences including the difference in the first unit, and when the accumulated differences reach a first predetermined value, add a second predetermined value to the second frequency in a second unit subsequent to the first unit, and subtract a third predetermined value from the accumulated differences in the second unit. The unit can be a period of P1, P2, . . . , P7. The first predetermined value can be 0.5 or −0.5. The second predetermined value can be 1 or −1. The third predetermined value can be 1 or −1. The determining of the second resolution can be obtained by rounding the first resolution, the rounding including rounding off, rounding up, or rounding down a digit after a decimal point of the first resolution. The second resolution can be set to a unit of the period of the horizontal line. The at least one processor 4 can be configured not to add a second predetermined value to the second frequency in a second unit subsequent to the first unit, and not to subtract a third predetermined value from the accumulated differences in the second unit when the accumulated differences doesn't reach a first predetermined value. The first and the second unit can be a period of a line of an image sensor 242, a period of a light emitting line.

(Effects)

Now, the following conditions are supposed, for example.

Vocal cord vibration frequency [Hz] (MAX)=1000 Hz

Slow-motion frequency (MIN)=0.5 Hz

In this case, the cycle difference between the vocal cord cycle and the pulsed light cycle is 500 ns as shown in the equation below.

$$1/(1000 \text{ Hz} - 0.5 \text{ Hz}) - 1/1000 \text{ Hz} = 500 \text{ ns}$$

In addition, it is supposed that the image pickup apparatus 24 performs image pickup under the following conditions.

Horizontal line frequency=67500 Hz

Frame rate=60 Hz

Vertical resolution=1125 horizontal lines

Under the above-described conditions, the difference between the actual light emission cycle and the ideal light emission cycle for 1 pulsed light is smaller than 1 horizontal line period, that is, becomes 14814 ns (=1/(60×1125)) to the maximum, in some cases. In other words, only extremely low precision can be achieved, compared to the precision of the ideal cycle difference of 500 ns.

In contrast, in the present embodiment, based on the dynamic visual acuity of the human eyes, the accumulated error is maintained within the predetermined range, supposing that a sufficient precision can be achieved as long as an error in a period during which about 100 pulsed lights are generated, for example, falls within the predetermined range. As a result, even if the period during which 100 pulsed lights are generated elapses, the error between the actual light emission cycle and the ideal light emission cycle can be smaller than 1 horizontal line period. In the above-described example, the average accumulated error of the 100 pulsed lights is about 148 ns (=14814 ns/100), and the precision which is about 30% of the ideal cycle difference of 500 ns can be achieved.

Thus, in the present embodiment, in the light emission control of a light source that illuminates the object with the pulsed light by emitting the pulsed light, with 1 horizontal line cycle of the image pickup apparatus as a minimum temporal resolution, the light emission cycle is calculated with the temporal resolution (decimal precision) which is more precise than the minimum temporal resolution (integer precision), the pulsed light is emitted in a cycle formed into an integer by rounding off the digits after the decimal point of the cycle calculated with the highly-precise resolution, the error between the cycle calculated with the highly-precise resolution and the rounded cycle obtained with the integer precision is accumulated, and when the accumulated error reaches the predetermined range, the rounded cycle obtained with the integer precision is increased or decreased by 1 horizontal line period, and thereby the accumulated error is reduced. With such a configuration, an average error when observation is performed with a plurality of pulsed lights can be reduced, to thereby enable smooth slow-motion observation with the human eyes.

Note that, in the above-described embodiment, the minimum temporal resolution of the actual light emission cycle of the pulsed light is set to 1 horizontal line period. However, the minimum temporal resolution of the pulsed light may be set to be smaller than 1 horizontal line period (1 horizontal line period×decimal). In this case, the minimum temporal resolution of the ideal light emission cycle of the pulsed light is set to a higher precision than the minimum temporal resolution of the actual light emission cycle of the pulsed light.

Second Embodiment

Figure 5:
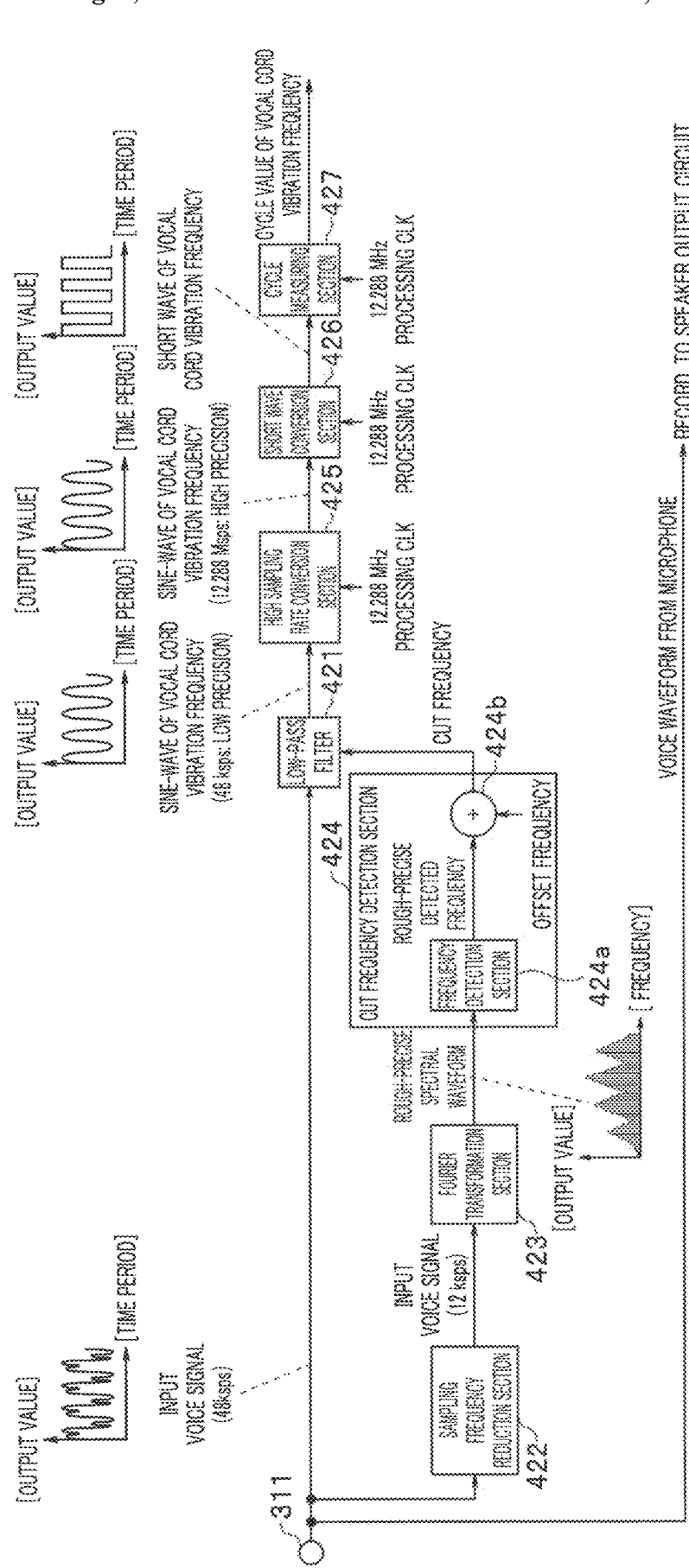
FIG. 5 is a block diagram showing a second embodiment of the present disclosure.

FIG. 5 is a block diagram showing a second embodiment of the present disclosure. The present embodiment shows one example of a specific configuration of the vibration frequency detection section 42 in FIG. 1, and enables the voice frequency to be detected with high precision using a small amount of arithmetic operation. Note that other hardware configurations in the present embodiment are the same as those in the first embodiment.

In a vocal cord diagnosis, the light emission timings of the pulsed lights are determined based on the vocal cord vibration frequency of the patient. As described above, the voice input apparatus 3 acquires voice based on the vocal cord vibration, and the vibration frequency detection section 42 calculates the frequency of the voice based on the vocal cord vibration (vocal cord vibration frequency). In order to properly controls the light emission timing of the pulsed lights, calculation of the accurate vocal cord vibration frequency is required.

Figure 6:
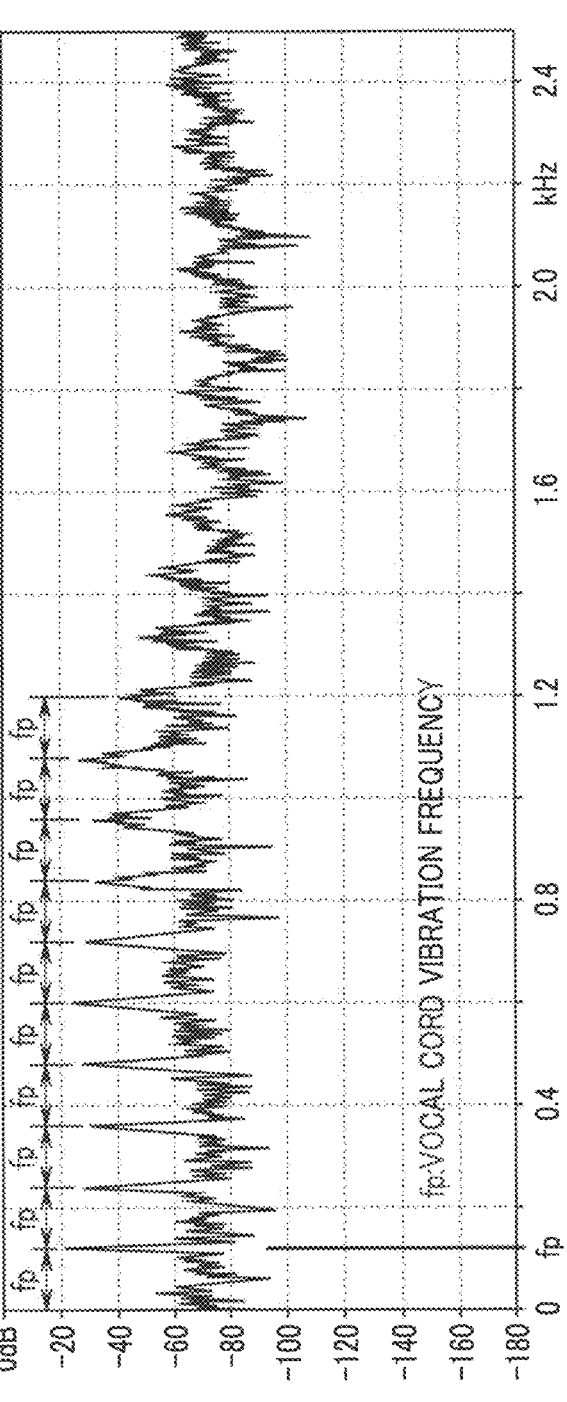
FIG. 6 is a waveform diagram showing a frequency spectrum of voice, with frequency on a horizontal axis and power on a vertical axis.

FIG. 6 is a waveform diagram showing a frequency spectrum of voice, with frequency on a horizontal axis and power on a vertical axis. In a vocal cord diagnosis, the subject to be examined is generally asked to produce a vowel sound. In this case, as shown in FIG. 6, the voice based on the vocal cord vibration is a synthesized wave of a plurality of waves with peaks at the fundamental frequency of the frequency fP and its multiplied frequency.

The vibration frequency detection section 42 receives such a voice which is the synthesized wave. Fourier transformation (FFT) is applied to the voice, to thereby enable a spectral waveform to be obtained and the fundamental frequency of the fundamental frequency wave (fundamental wave), i.e., the vocal cord vibration frequency to be extracted. However, when the vocal cord vibration frequency is directly extracted from the spectral waveform by Fourier transformation, the amount of arithmetic operation of the Fourier transformation is enormous. This causes problems such as an increase in the chip size and a heat generation amount.

For example, the performance required for FFT is obtained under the following conditions.

Sampling frequency of voice: 48000 Hz

Detection precision: 0.1 Hz

In this case, the amount of arithmetic operation of FFT (size of the frequency axis by Fourier transformation) is a power of 2 including 48000 Hz/0.1 Hz=480,000, that is, 524,288 (19th power of 2), which is an extremely large amount of arithmetic operation.

In view of the above, in the present embodiment, filter processing is performed to extract the fundamental wave. Then, Fourier transformation is performed for calculating a cut-off frequency of the filter processing, to thereby enable highly-precise detection of the voice frequency even in the case where rough-precise Fourier transformation is employed to reduce the amount of arithmetic operation. In other words, the Fourier transformation employed in the present embodiment does not require the amount of arithmetic operation that satisfies the above-described required detection precision of 0.1 Hz, but may have a precision for achieving the filter processing.

In FIG. 5, the vibration frequency detection section 42 receives an input of a voice signal from the voice input apparatus 3 through the connector 311. The sampling frequency of the voice signal is 48 ksps (sample per second), for example. The voice signal inputted through the connector 311 is supplied to a low-pass filter 421, and also to a sampling frequency reduction section 422. The sampling frequency reduction section 422, a Fourier transformation section 423, and a cut frequency detection section 424 detect the cut frequency of the low-pass filter 421.

The sampling frequency reduction section 422 can be configured by a 4-tap FIR filter, for example. The sampling frequency reduction section 422 reduces the sampling frequency of the input voice signal. For example, the sampling frequency reduction section 422 reduces the sampling frequency of the voice signal to 12 ksps.

The voice signal from the sampling frequency reduction section 422 is supplied to the Fourier transformation section 423. The Fourier transformation section 423 performs the Fourier transformation processing on the inputted voice signal to obtain the spectral waveform of the input voice signal. In the present embodiment, the sampling frequency of the voice signal inputted to the Fourier transformation section 423 is reduced, and enables the amount of the arithmetic operation of the FFT arithmetic operation to be reduced.

The processor can be configured to perform Fourier transformation processing on a signal of the vibration frequency of the object to obtain a first fundamental frequency of the vibration, and cut the first fundamental frequency from the signal to obtain a second fundamental frequency being more precise than the first fundamental frequency. The processor can be configured to determine validity of a frequency interval of respective peaks obtained by the Fourier transformation processing, and determine the fundamental frequency based on the determined validity.

Now, it is supposed that the range of the detection target (vocal cord vibration frequency) is 50 Hz to 1000 Hz. In other words, the minimum frequency to be detected is 50 Hz and the frequency of the double wave thereof is 100 Hz. If the cut frequency can be set between 50 Hz and 100 Hz, the voice signal of 50 Hz can be extracted by the filter processing.

The cut frequency may be set at any position between 50 Hz and 100 Hz, but the cut frequency is set with the precision of 10 Hz (=50 Hz×20%), allowing for a margin of about 20%. Note that in the case where the frequency to be detected is higher, a more leeway is provided. If the cut frequency can be set with the precision of 10 Hz, all frequencies to be detected can be handled.

In other words, the following condition has only to be satisfied: (sampling frequency 12 kHz/precision of 10 Hz of the cut frequency)<size of the amount of the arithmetic operation (size of the FFT frequency axis). For example, the size is set to 2,048. The size is 12 kHz/2048=5.859375 Hz, which is a value within the precision of 10 Hz. Note that this size is a size of $\frac{1}{256}$ of the size of 524,288 obtained directly by the Fourier transformation, which is 1/65536 (=256 squared) when converting into the amount of arithmetic operation, indicating that the amount of arithmetic operation can be extremely small.

The spectral waveform obtained by the Fourier transformation section 423 is supplied to a frequency detection section 424a of the cut frequency detection section 424. The frequency detection section 424a detects the fundamental wave by the following processing steps (i) to (iv).

(i) Detect the local maximum values (peaks) p0, p1, p2, . . . and the frequencies thereof (peak frequencies) fp0, fp1, . . . by comparing the magnitude of the powers at the frequency positions of the spectral waveform.

(ii) Sort the detected peak frequencies in an ascending order. Note that the order is fp0<fp1<fp2<fp3

(iii) Determine the validity of the interval of the peak frequencies by applying the following equation to the smallest frequency fp0. If the equation is established, it is determined that there is validity, fp0 is set as the fundamental wave frequency of the fundamental frequency.

fp1≈afp0, fp2≈bfp0, fp3≈cfp0, fp4≈dfp0 (a, b, c, and d are integers) (iv) If (iii) is not established, p0 is excluded from the peak candidate, (iii) is performed on the frequency fp1 of peak p1, which has the next smallest frequency, to determine whether (iii) is established.

Thereafter, the same procedure is repeated until (iii) is established.

Note that the precision of the Fourier transformation section 423 is relatively low, it can be considered that the frequencies at the peak positions of the spectral waveform from the Fourier transformation section 423 do not accurately coincide with the vocal cord vibration frequency. However, there is no problem as long as the cut frequency used in the filter processing for extracting the fundamental wave of the frequency to be detected can be detected.

The frequency detection section 424*a* outputs the fundamental wave frequency obtained by the above-described processing steps (i) to (iv) to an adder section 424*b*. In the case where the minimum frequency to be detected is 50 Hz, if the precision is set to be 5.859375 Hz, the detection result by the frequency detection section 424*a* is 50±5.859375 Hz, and the frequency lower than 50 Hz may possibly be set as the cut frequency. The adder section 424*b* adds the predetermined offset frequency and adjusts such that the cut frequency is set between the minimum frequency and the frequency of the double wave. For example, when the minimum frequency to be detected is 50 Hz, the offset frequency is set to 25 Hz. In this example, the offset frequency of about 75 Hz is supplied from the cut frequency detection section 424 to the low-pass filter 421.

The low-pass filter 421 performs bandwidth limiting on the voice signal inputted through the connector 311, by using the cutoff frequency. Then, the fundamental wave of the inputted voice signal, that is, a sine-wave of the vocal cord vibration frequency can be obtained from the low-pass filter 421. Note that an IIR filter can be employed as the low-pass filter 421, a Butterworth filter or a Lanczos filter may be employed, for example. The output of the low-pass filter 421 is supplied to a high sampling rate conversion section 425.

In order to improve the temporal resolution of the frequency (cycle) to detect, the high sampling rate conversion section 425 performs high sampling rate conversion processing on the voice signal sampled at a low sampling rate of 48 KHz. For example, the high sampling rate conversion section 425 may use a clock with a higher frequency than the sampling frequency and perform linear approximation by using a first-order hold to perform the high sampling rate conversion. The output of the high sampling rate conversion section 425 is supplied to a rectangular wave conversion section 426.

If the required detection precision of 0.1 Hz is expressed in terms of the temporal precision, it is 100 ns (=1/(1000 Hz−0.1 Hz)−(1/1000 Hz)), which requires a high-speed clock of 10 MHz (=1/100 ns) or more. The high sampling rate conversion section 425, for example, may employ a clock of 12.288 MHz which is a frequency of 256 times of 48 kHz. Note that, since the high sampling rate conversion section 425 multiplies the temporal precision by 256, the output level is also linearly approximated by adding precision of 256 times (8 bits) or more.

In order to detect the cycle to be detected, the rectangular wave conversion section 426 converts the inputted high sampling rate voice signal into a rectangular wave by binarization. The output of the rectangular wave conversion section 426 is supplied to a cycle measuring section 427.

The cycle measuring section 427 measures the cycle of the rectangular wave from the rectangular wave conversion section 426. For example, the cycle measuring section 427 may measure the cycle by counting the rising of the rectangular wave to the next rising of the rectangular wave. The cycle measuring section 427 outputs the value of the obtained cycle value or the frequency calculated from the obtained cycle value.

Thus, in the present embodiment, the rough-precise Fourier transformation is employed to obtain the cut frequency, the cut frequency is used to extract the fundamental wave by the filter processing, and the voice frequency is obtained at a high precision. The rough-precise Fourier transformation can thus be employed, to thereby be capable of remarkably reducing the arithmetic operation amount.

Third Embodiment

Figure 7:
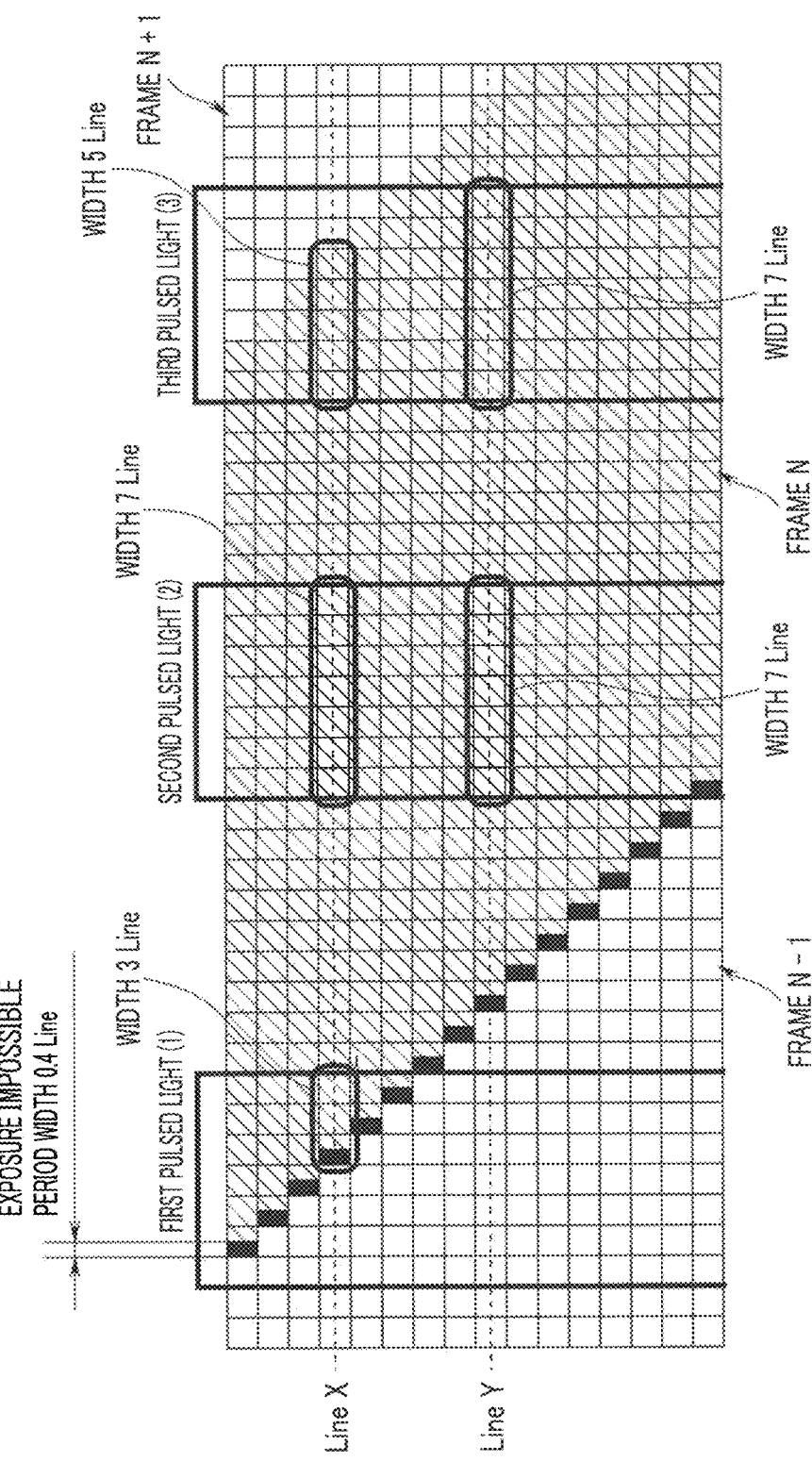
FIG. 7 is explanatory view showing a third embodiment of the present disclosure.

FIG. 7 is explanatory view showing a third embodiment. Other hardware configurations in the present embodiment are the same as those in the first embodiment.

In the above-described first embodiment, the electronic shutter of the image pickup device is fully open, and the processing has been shown assuming that the light emission amount is proportional to the exposure amount. However, actually, an exposure impossible period such as a readout period exists. In the present embodiment, such an exposure impossible period is taken into consideration, to obtain the illumination time pixel signals. During the exposure impossible period, the image sensor may not be read out.

In also the present embodiment, the image processing section 45 performs the above-described synthesizing arithmetic operation, to generate the illumination time pixel signals from the pixel signals of a plurality of consecutive frames stored in the memory 46. As described above, the synthesizing arithmetic operation is an arithmetic operation in which one pulsed light in one frame is selected as a selected pulse, and the synthesizing ratio between the all-pulse exposure amount and the selected-pulse exposure amount is used for each horizontal line. In the present embodiment, the all-pulse exposure amount and the selected-pulse exposure amount are obtained by taking the exposure impossible period into consideration. In other words, in the present embodiment, correction for reducing the all-pulse exposure amount and the selected-pulse exposure amount by an amount corresponding to the exposure impossible period is performed. In other words, if the light emission overlaps the exposure impossible period such as the readout period, the image processing section 45 performs gain correction on the output value which is on the assumption that exposure has been performed in the exposure impossible period.

FIG. 7 shows one example of the exposure and the readout timing in the same description manner as that in FIG. 3. The bold frames in FIG. 7 show the first pulsed light (1), the second pulsed light (2), and the third pulsed light (3) from the illumination light generation apparatus 5. In FIG. 7, one square in the horizontal axis represents 1 horizontal line period, and one square in the vertical axis represents each of the horizontal lines. The painted-out parts in FIG. 7 represent the exposure impossible period such as the readout period, and the exposure impossible period is 0.4 Line (horizontal line period) in the example in FIG. 7.

In the present embodiment, the image processing section 45 performs the synthesizing arithmetic operation shown by the following equations (3) to (6) for a case where dimming is performed and a case where dimming is not performed, to obtain the illumination time pixel signal. Note that the pixel value of the Xth horizontal line in the frame N is denoted by Vpx, and the pixel value of the Yth horizontal line in the frame N is denoted by Vpy.

In the case where dimming is not performed, when the light emission period of the pulsed light does not overlap the exposure impossible period as in the Yth line (Line Y), for example, the image processing section 45 performs the synthesizing arithmetic operation in the following equation (3).

$$\text{Illumination time pixel signal of the frame } N = \{7/(7+7)\} \times Vpy \quad (3)$$

In the case where dimming is not performed, when the light emission period of the pulsed light overlaps the exposure impossible period as in the Xth line (Line X), for example, the image processing section 45 performs the synthesizing arithmetic operation in the following equation (4).

$$\text{Illumination time pixel signal of the frame } N = \qquad (4)$$
$$\left[ \{7/(7+7)\} \times \{(3+7+5)/(3-0.4+7+5)\} \right] \times Vpx$$

In the case where dimming is performed, since it can be considered that the light amounts of the respective pulsed lights may be different, the synthesizing arithmetic operation is performed by taking the light amounts of the respective pulsed lights into consideration. It is assumed that the light amounts of the first pulsed light (1) to the third pulsed light (3) are La1 to La3, respectively.

In the case where dimming is performed, when the light emission period of the pulsed light does not overlap the exposure impossible period as in the Yth line (Line Y), for example, the image processing section 45 performs the synthesizing arithmetic operation in the following equation (5).

$$\text{Illumination time pixel signal of the frame } N = \qquad (5)$$
$$\left[ \{7La2/(7La2+7La3)\} \times Vpy \right]$$

In the case where dimming is performed, when the light emission period of the pulsed light overlaps the exposure impossible period as in the Xth line (Line X), for example, the image processing section 45 performs the synthesizing arithmetic operation in the following equation (6).

$$\text{Illumination time pixel signal of the frame } N = \qquad (6)$$
$$\left[ \{7La2/(3La1+7La2+5La3)\} \times \right.$$
$$\left. \{(3La1+7La2+5La3)/(3La1-0.4La1+7La2+5La3)\} \right] \times Vpx$$

Note that description has been made on the example of the rolling-shutter method. In the case of a global shutter sensor, determination and correction may be performed for each field or frame.

Thus, in the present embodiment, the synthesizing arithmetic operation is performed by taking the exposure impossible period into consideration, and thereby the illumination time pixel signals can be obtained at the high precision, and exposure uneveness can be corrected more surely.

Fourth Embodiment

Next, the fourth embodiment will be described. Other hardware configurations in the present embodiment are the same as those in the first embodiment.

In the first embodiment, one pulsed light in one frame is selected as a selected pulse and an illumination time pixel signal using the selected pulse is obtained. If the duty ratio of the pulsed light is fixed, the higher the light emission frequency, the shorter the light emission period of one shot of pulsed light, and the higher the frequency, the smaller the output value of the generated image. In other words, the output value of the generated image changes depending on the light emission frequency. This causes a problem that, during the vocal cord observation, the pulsed light frequency fluctuates depending on the fluctuation of the frequency of a voice, and the brightness of the observation image fluctuates.

In the first embodiment, the pulsed light is generated for a plurality of times in the one frame period, to perform a plurality of times of exposures (multiple exposures). If the light emission period of the pulsed light (the pulse width from the rising to the falling of the pulsed light) is fixed, the lower the light emission frequency, the smaller the number of times of the multiple exposures, which results in a decrease of the total exposure amount (time) and deterioration of S/N of the sensor output image (total exposure). This also causes a problem that the noise amount of the observation image fluctuates if the frequency of the voice fluctuates during the observation.

In the present embodiment, the brightness and the S/N are stabilized regardless of the fluctuation of the light emission frequency, for example, the fluctuation resulting from the fluctuation of the vocal cord vibration frequency during the vocal cord observation. For example, the light source control section 431 controls the light source driver 52 to generate the pulsed light at a fixed duty ratio. In addition, the image processing section 45 multiplies the illumination time pixel signal by a gain proportional to the number of times of multiple exposures.

The number of times of multiple exposures can be expressed by (light emission frequency [Hz]/frame frequency [Hz] of the image pickup device). The image processing section 45 performs correction arithmetic operation of (illumination time pixel signal)×(number of times of multiple exposures) for each frame to obtain an image output stable in the brightness and S/N.

Note that the output of the image pickup device is the image obtained by multiple exposures with all pulsed lights, and even if the image is multiplied by multiple exposure times gain, the image does not have an S/N problem. In addition, since the uneveness has been removed from the illumination time pixel signals by the synthesizing arithmetic operation, the image processing section 45 calculates the number of times of multiple exposures once per one frame, and performs a common correction arithmetic operation for all the lines once in one frame. The image output after the correction arithmetic operation does not depend on the light emission frequency, which results in stable brightness and S/N.

However, even if the image processing section 45 performs the correction arithmetic operation using the number of times of the multiple exposures, the brightness may sometimes fluctuate due to the light emission frequency. In the first embodiment, in order to suppress the amount of arithmetic operation, the temporal resolution of the pulsed lights is limited to the 1 horizontal line cycle. With such a limitation, the duty ratio of the pulsed light sometimes cannot be set to a target value.

In the present embodiment, the image processing section 45 further performs gain correction on the error between the target duty ratio and the duty ratio in the actual driving. The correction gain in this case can be expressed by (target duty ratio)/(actual duty ratio).

For example, illumination and image pickup are performed under the following conditions.

Light emission frequency=1000 Hz

Frame rate of image pickup=60 Hz, vertical resolution (number of horizontal lines)=1125 Lines Light emission cycle=68 Lines Note that the light emission cycle can be obtained by rounding off the result obtained by the equation of 1125 Lines×60 Hz/1000 Hz=67.5 Lines. Note that the error caused by the rounding off is corrected in the first embodiment, which is not a concern here.

Target duty ratio=10%

Light emission period=7 Lines

Note that the light emission period is obtained by rounding off the result obtained by the equation of 68 Lines×10%=6.8 Lines.

As a result, the actual duty ratio can be calculated as 10.294% (=7 Lines/68 Lines).

In this case, the image processing section 45 calculates a final output image for each one frame by the following equation.

$$(\text{final output image}) = (\text{illumination time pixel signal}) \times$$
$$(\text{number of times of multiple exposures}) \times (10\%/10.294\%)$$

Even in the case where the temporal resolution of the pulsed light is limited to 1 horizontal line cycle in order to suppress the amount of arithmetic operation, the fluctuations in the brightness and the S/N can be avoided.

Thus, in the present embodiment, an output image stable in the brightness and S/N can be obtained regardless of the fluctuation of the light emission frequency of the pulsed light.

(Display Control)

Figure 8:
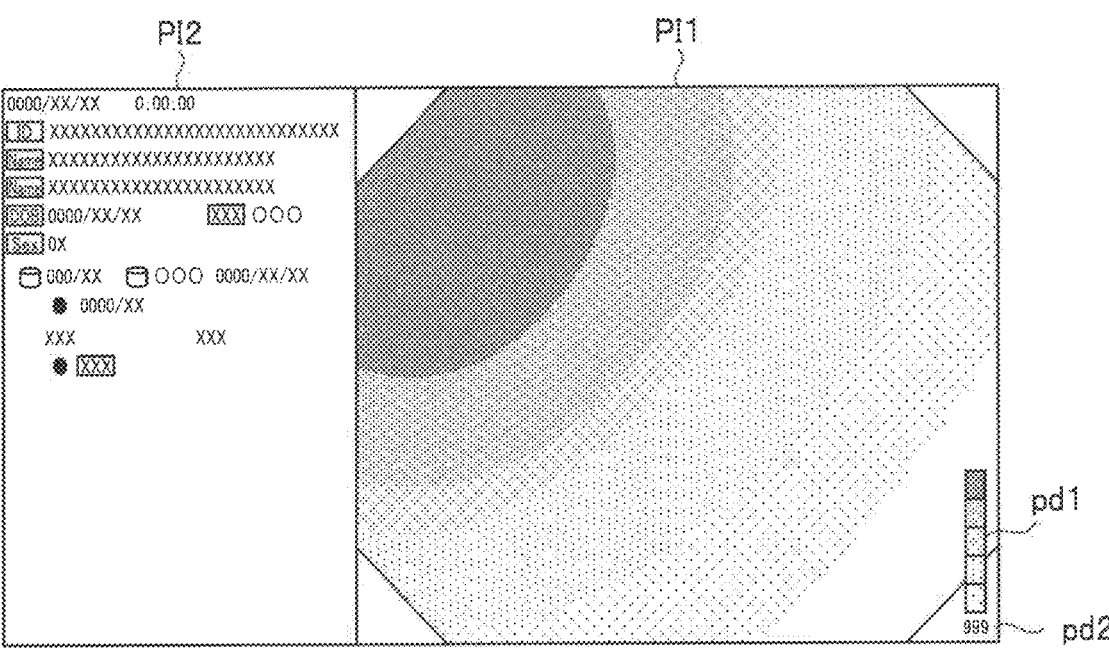
FIG. 8 is an explanatory view showing a display example on a display screen of a display apparatus 6.
Figure 9:
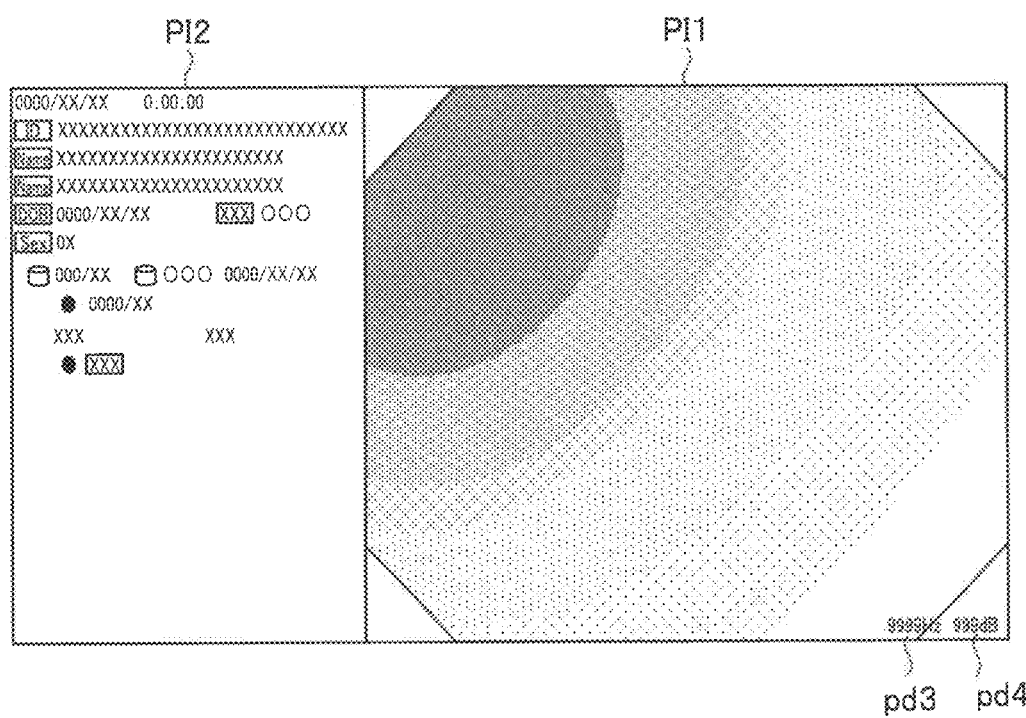
FIG. 9 is an explanatory view showing a display example on the display screen of the display apparatus 6.

FIGS. 8 and 9 are explanatory views each showing a display example on a display screen of the display apparatus 6.

The display control section 47 in each of the embodiments outputs the display data to the display apparatus 6, to thereby enable not only an endoscopic image but also various kinds of information to be displayed. For example, as shown in FIG. 8 and FIG. 9, the display control section 47 can display on the display screen of the display apparatus 6, the endoscopic image in an endoscopic image region PI1, and various kinds of information in an information display region PI2. Furthermore, the display control section 47 enables a pseudo color display pd1 and an average value display pd2 to be displayed in the endoscopic image region PI1 as shown in FIG. 8, and enables a frequency display pd3 in a stroboscopic observation and a voice level display pd4 to be displayed in the endoscopic image region PI1 as shown in FIG. 9 (hereinafter, these displays pd1 to pd4 are referred to representatively as a GUI display pd).

The display control section 47 has a function of updating character information in the GUI display pd in conjunction with the endoscopic image that is being displayed. In addition, the display control section 47 has a function of freezing the endoscopic image and the character information. However, due to the constraint of the product performance, the display control section 47 updates the character information in non-real time but periodically, which may cause a discrepancy between the endoscopic image and the contents of the character information when the endoscopic image and the character information are frozen.

In view of the above, in the present embodiment, when an instruction for the execution of the function of freezing the endoscopic image and the character information is given, the control section 43 controls the display control section 47 so as to perform the freezing processing after updating the character information associated with the endoscopic image. The freezing processing is performed after the GUI display pd has been updated, which results in correspondence between the endoscopic image and the contents of the character information.

Figure 10:
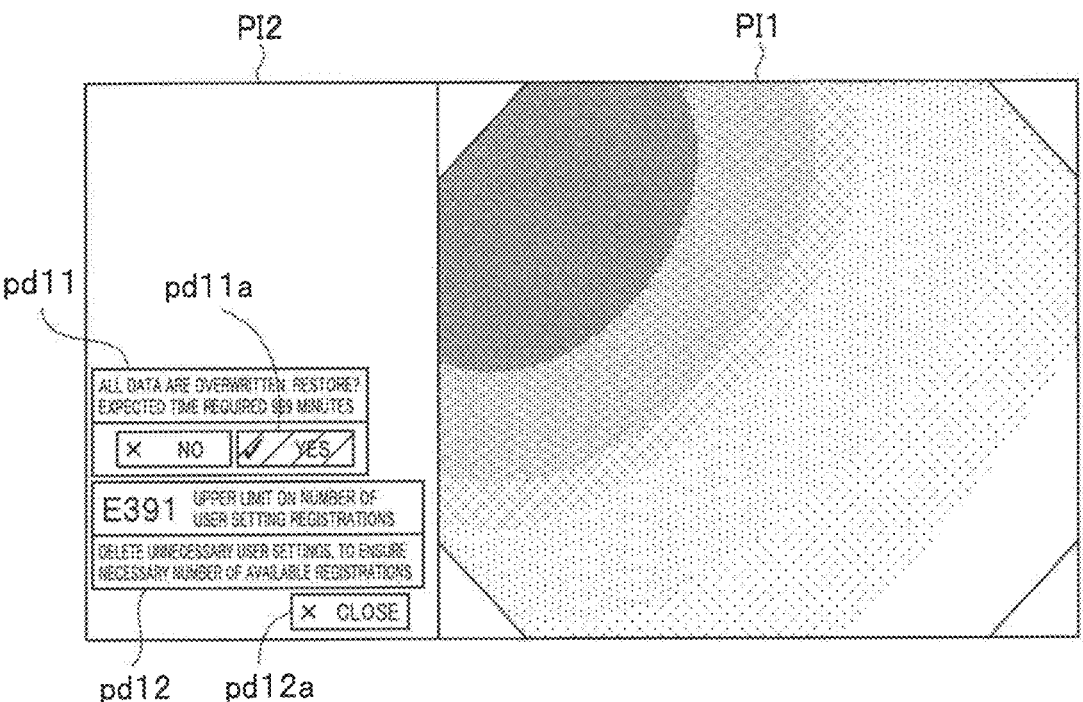
FIG. 10 is an explanatory view showing another display example on the display screen of the display apparatus 6.
Figure 11:
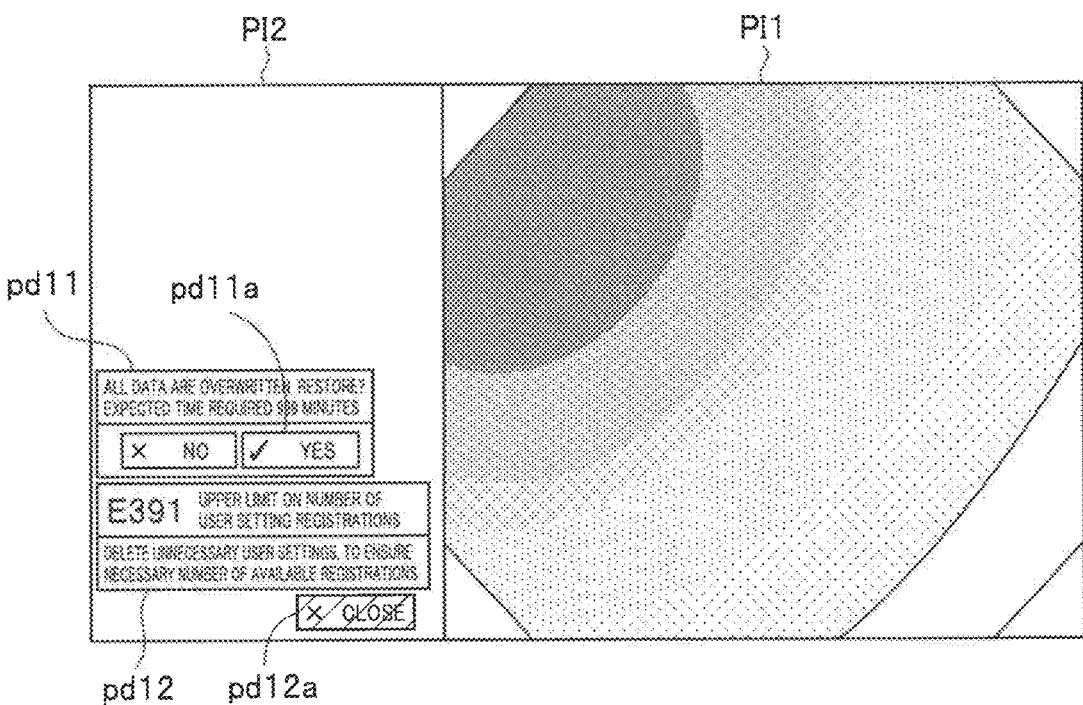
FIG. 11 is an explanatory view showing another display example on the display screen of the display apparatus 6.

FIGS. 10 and 11 are explanatory views each showing another display example on the display screen of the display apparatus 6.

As shown in FIGS. 10 and 11, the display control section 47 causes the endoscopic image to be displayed in the endoscopic image region PI1, and the various kinds of information to be displayed in the information display region PI2. In FIGS. 10 and 11, message displays pd11 and pd12 are displayed as the information displayed in the information display region PI2.

The message display pd11 includes a "No" button and "Yes" button pd11a. In addition, the message display pd12 includes "Close" button pd12a. Thus, a plurality of message displays pd11, pd12 can be displayed simultaneously in the information display region PI2. In addition, when the display control section 47 displays the message display pd11 and the message display pd12, a cursor can be arranged on various kinds of buttons. In this case, if it is supposed that the display control section 47 generally displays the message display pd11, and thereafter displays the message display pd12, the cursor is arranged on the button in the message display pd11 displayed first. FIG. 10 shows a state where the cursor selects the button "Yes" pd11a by showing the "Yes" button pd11a with oblique lines.

If the necessity to operate the button in the message display pd12 is high, in other words, a priority of a response to an inquiry of the message display pd12 is higher than a priority of a response to an inquiry of the message display pd11, the cursor can be brought into a state of selecting the "Close" button pd12a.

The display control section 47 stores priority information in the memory 46 or a memory not shown, and when the plurality of message displays are displayed, the cursor is set to a state of selecting the button in the message with higher priority. FIG. 11 shows this state, and when the message displays pd11, pd12 are displayed simultaneously, the cursor is arranged so as to be in the state of selecting the "Close" button pd12a in the message display pd12 with higher priority, regardless of the display order of the message displays pd11, pd12. The oblique lines of the "Close" button pd12a in FIG. 11 show the state where the cursor is in the state of selecting the "Close" button pd12a.

Thus, in the present embodiment, the cursor is automatically arranged at a position where the cursor selects the message with the highest priority among the plurality of messages. Thereby, the operability is improved.

(Recording Control)

Figure 12:
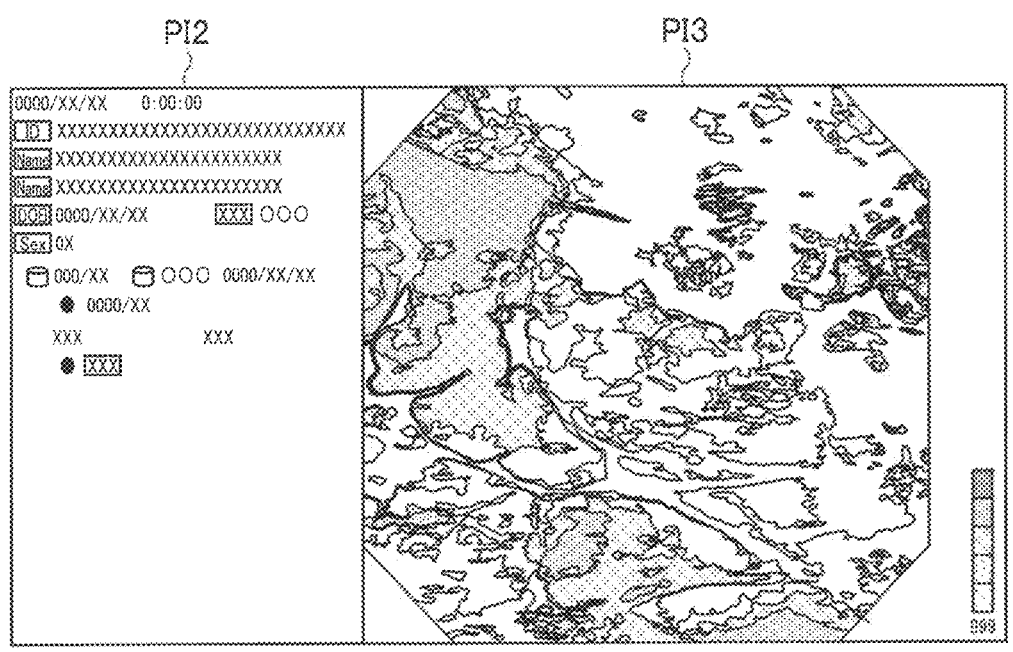
FIG. 12 is an explanatory view showing an endoscopic image in a pseudo color display.

FIG. 12 is an explanatory view showing an endoscopic image in the pseudo color display.

As shown in FIG. 12, the display control section 47 in each of the embodiments can display the endoscopic image region in the pseudo color display in a pseudo color display region PI3 on the display screen of the display apparatus 6. The recording control section 49 can record a still image of the normal endoscopic image obtained by image processing by the image processing section 45 and a still image of the endoscopic image in the pseudo color display. However, when both of these still images are recorded, recording operation has to be performed twice, which has resulted in complexity.

In view of the above, in the present embodiment, when there is an endoscopic image displayed in the pseudo color by the display control section 47, the control section 43 controls the recording control section 49 so as to record the still images of both of the normal endoscopic image and the endoscopic image in the pseudo color display by a single recording operation.

Such a configuration enables the normal endoscopic image and the endoscopic image in pseudo color display to be recorded by a single recording operation.

(Suction Structure)

Figure 13:
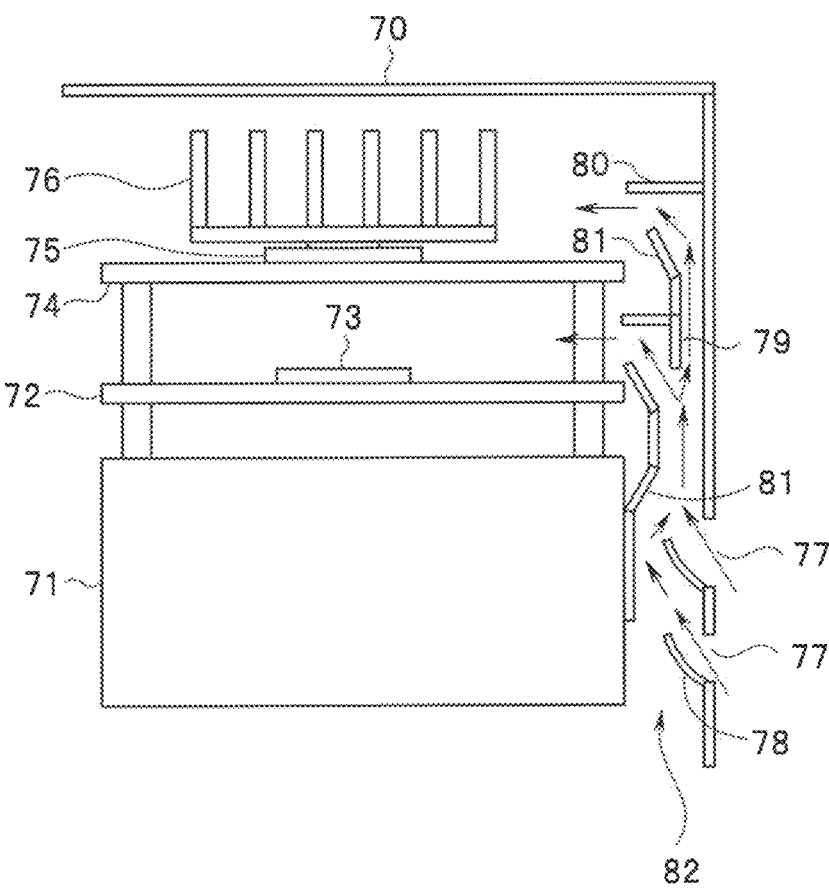
FIG. 13 is an explanatory view showing one example of a suction structure of a processor.
Figure 14:
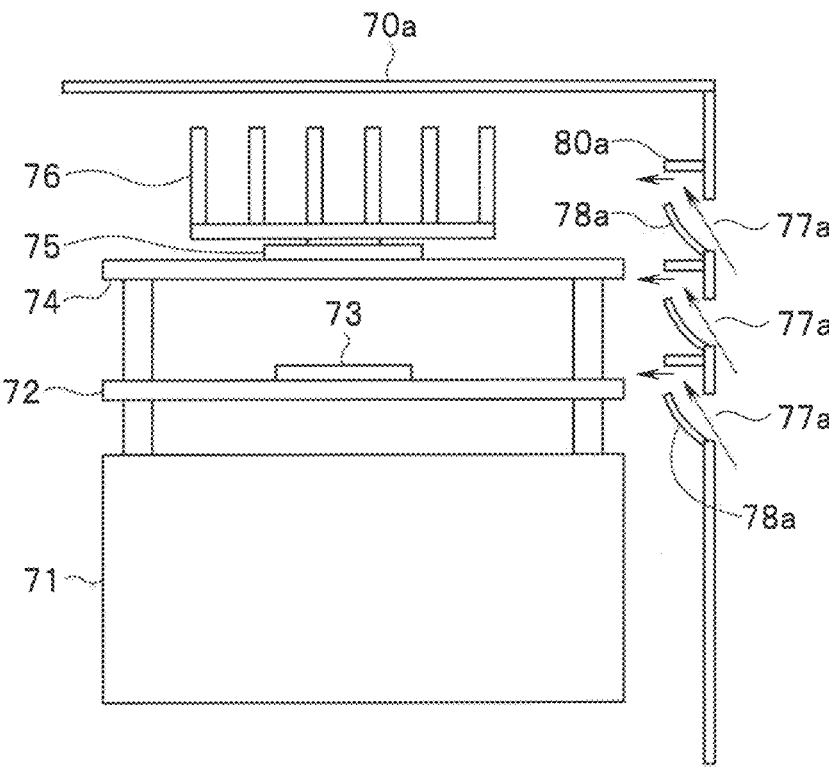
FIG. 14 is an explanatory view showing a suction structure in a comparative example.

FIG. 13 is an explanatory view showing one example of a suction structure of a processor employed in the present embodiment. FIG. 14 shows a suction structure in the comparative example. In FIG. 13 and FIG. 14, the same constituent elements are attached with the same reference signs and descriptions thereof will be omitted.

In FIG. 13 and FIG. 14, for example, a substrate 72 and a substrate 74 are disposed in multilayer form on a supporting section 71 in the processor 4. A cooling object member 73 such as a CPU is arranged on the substrate 72, and a cooling object member 75 such as a CPU is arranged on the substrate 74. A heat sink 76 is attached to the cooling object member 75.

In the comparative example in FIG. 14, the cooling object members 73, 75 are arranged in a housing 70a. The housing 70a includes a plurality of intake ports 77a, and a flow regulating plate 80a, which is provided above the intake ports 77a, on the side wall of the housing on which the intake ports 77a are open. Each of the intake ports 77a includes a slatted shutter 78a. As shown by the arrows, the slatted shutter directs the flow of air toward the direction of the flow regulating plate 80a when the outside air is taken into the housing 70a. The air introduced into the housing 70a advances toward the cooling object members 73, 75 by the flow regulating plate 80a, to cool the cooling object members 73, 75.

The housing 70a incorporates a fan, not shown, and with the intake and exhaust function of the fan, the air sucked from the intake ports 77a is distributed in the housing 70a and flowed out from an exhaust port, not shown. The suction structure in the comparative example is arranged in the vicinity of the cooling object, and has a slatted shutter shape that is configured to prevent water from entering inside of the housing 70A even when the housing 70A is splashed with water and to prevent the internal structure from being visible.

However, in recent years, the air velocity of the suction has increased due to the increased internal power consumption, which leads to easy intrusion of water from the intake ports, and there has been a concern that the water intrudes inside to damage the components.

In view of the above, as shown in FIG. 13, the housing 70 in the present embodiment includes the intake ports 77 provided on the side wall of the housing so as to be located at the positions sufficiently lower than the substrates 72, 74 on which the cooling object members 73, 75 are mounted. Each of the intake ports 77 includes a slatted shutter 78 similar to that in the comparative example, and the air sucked from the intake ports 77 advances upward in the housing 70.

In the example in FIG. 13, a flow regulating plate 81 is provided opposed to the side wall of the housing on which the intake ports 77 are provided. The flow regulating plate 81 configures a duct structure 82 that allows air to distribute between the flow regulating plate and the side wall of the housing. In the vicinity of the position corresponding to the cooling object member 73 in the height direction of the housing 70, a branch plate 79 is formed, and the branch plate 79 branches the air flow passage formed by the duct structure 82 into the cooling object member 73 side and the upper side of the housing 70. In addition, in the vicinity of the position corresponding to the cooling object member 75 in the height direction of the housing 70, a flow regulating plate 80 is provided on the side wall of the housing, and the flow regulating plate 80 is configured to direct the air flowed through the duct structure 82 toward the cooling object member 75 side.

Thus, in the example in FIG. 13, the intake ports 77 are provided at the positions sufficiently lower than the components which might be damaged when water is splashed on them, to thereby surely prevent water from being splashed on the cooling object members 73, 75, and other components. In addition, the duct structure 82 enables the air entered from the intake ports 77 to flow upward toward the cooling object members 73, 75. Furthermore, the duct structure 82 includes a branch plate 79, and enables the air to distribute to the plurality of cooling objects.

Thus, in the example in FIG. 13, even if the air velocity of the suction has increased to lead to easy intrusion of water from the intake ports, it is possible to surely prevent water from being splashed on the plurality of cooling objects, to thereby enable these plurality of cooling objects to be cooled surely.

The present disclosure is not limited to the above-described embodiments as they are, and it goes without saying to embody the disclosure by modifying the constituent elements in a range without departing from the gist of the disclosure at the practical stage. In addition, various disclosures can be achieved by appropriately combining the plurality of constituent elements disclosed in each of the above-described embodiments. Some of the constituent elements may be deleted from all the constituent elements shown in the embodiments, for example. Furthermore, constituent elements over different embodiments may be appropriately combined.

Many of the above-described techniques described above can be set by a program, and the above-described control and functions can be implemented by the program being read and executed by a computer. The entirety or a part of the program can be recorded or stored as a computer program product in a portable medium such as a flexible disk, CD-ROM, a non-volatile memory, or the like, or a storage medium such as hard disk, a volatile memory, or the like. The program can be distributed or provided at the time of product shipment, or through a portable medium or a communication line. It is possible for a user to easily implement the present embodiments by downloading the program through a communication network to install the program into a computer, or installing the program from a recording medium into the computer.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

Example 1. A light source apparatus comprising
a processor configured to control a light source that generates pulsed light with which an object is illuminated, and cause the light source to generate the pulsed light with a first temporal resolution,
the processor being configured to:
calculate, based on a vibration frequency of the object, a light emission cycle of the pulsed light with a second temporal resolution which is more precise than the first temporal resolution;
round the light emission cycle calculated with the second temporal resolution to a precision of the first temporal resolution, to set the light emission cycle obtained by the rounding as the light emission cycle of the pulsed light that is generated by the light source;
accumulate an error between the light emission cycle calculated with the second temporal resolution and the light emission cycle with the first temporal resolution that is calculated by the rounding;
increase the light emission cycle with the first temporal resolution in a unit of the first temporal resolution and decrease the accumulated error in the unit of the first temporal resolution, when the accumulated error reaches a predetermined positive value; and
decrease the light emission cycle with the first temporal resolution in the unit of the first temporal resolution and increase the accumulated error in the unit of the first temporal resolution, when the accumulated error reaches a predetermined negative value.

Example 2. The light source apparatus according to Example 1, wherein
the first temporal resolution is 1 horizontal line period of an image pickup device having a plurality of pixels that receive light from the object, to generate pixel signals, the object being illuminated with the pulsed light for a plurality of times in one frame.
Example 3. The light source apparatus according to Example 2, wherein
the rounding by the processor is to round off, round up, or round down a digit after a decimal point, to thereby set the light emission cycle of the pulsed light that is generated by the light source to a unit of the 1 horizontal line period.
Example 4. The light source apparatus according to Example 2, wherein
the processor is configured to increase the cycle of the pulsed light that is generated by the light source by the 1 horizontal line period when the accumulated error becomes 0.5 or more, and decrease the cycle of the pulsed light that is generated by the light source by the 1 horizontal line period when the accumulated error becomes −0.5 or less.
Example 5. The light source apparatus according to Example 1, wherein
the processor is configured to:
perform Fourier transformation processing on a signal based on a vibration of the object with a first precision, to obtain a fundamental frequency of the vibration;
perform filter processing, with the fundamental frequency of the vibration obtained by the Fourier transformation processing as a cut frequency, on the signal based on the vibration of the object; and
obtain, based on the signal after the filter processing, the fundamental frequency of the vibration with a second precision higher than the first precision.
Example 6. The light source apparatus according to Example 5, wherein
the processor is configured to determine the fundamental frequency based on a determination result of validity of a frequency interval of respective peaks obtained by the Fourier transformation processing performed with the first precision.
Example 7. An image pickup apparatus comprising:
an image pickup device including a plurality of pixels that receive light from an object, to generate pixel signals, the object being illuminated with pulsed light for a plurality of times in one frame;
a light source apparatus; and
a signal processing apparatus,
the light source apparatus and the signal processing apparatus including a processor,
the processor being configured to:
calculate, based on a vibration frequency of the object, a light emission cycle of the pulsed light with a second temporal resolution which is more precise than a first temporal resolution;
control a light source that generates the pulsed light so as to round the light emission cycle calculated with the second temporal resolution to a precision of the first temporal resolution and to set the light emission cycle obtained by the rounding as the light emission cycle of the pulsed light;
accumulate an error between the light emission cycle calculated with the second temporal resolution and the light emission cycle with the first temporal resolution that is obtained by the rounding;

increase the light emission cycle with the first temporal resolution in a unit of the first temporal resolution and decrease the accumulated error in the unit of the first temporal resolution, when the accumulated error reaches a predetermined positive value;

decrease the light emission cycle with the first temporal resolution in the unit of the first temporal resolution and increase the accumulated error in the unit of the first temporal resolution, when the accumulated error reaches a predetermined negative value;

receive, from the image pickup device, first pixel signals and second pixel signals, the first pixel signals being pixel signals for one frame read at a readout timing, at least a part of which includes an illumination period of the pulsed light, the second pixel signals being pixel signals for one frame read at a readout timing that is one frame after the readout timing of the first pixel signals, in an overlap line in which the illumination period of the pulsed light and the readout timing overlap with each other of the plurality of pixels, synthesize a pixel signal, which corresponds to the overlap line, among the first pixel signals and a pixel signal, which corresponds to the overlap line, among the second pixel signals, to generate pixel signals for one frame; and perform first gain correction on the synthesized pixel signals for the one frame by taking an exposure impossible period into consideration.

Example 8. The image pickup apparatus according to Example 7, wherein the processor is configured to, instead of the first gain correction, multiply the synthesized pixel signals for the one frame by a gain proportional to a number of multiple exposures with the pulsed light that occur during the one frame.

Example 9. The image pickup apparatus according to Example 7, wherein the first temporal resolution is 1 horizontal line period of an image pickup device having a plurality of pixels that receive light from the object, to generate pixel signals, the object being illuminated with the pulsed light for a plurality of times in one frame, and the processor is configured to perform, instead of the first gain correction, gain correction on the synthesized pixel signals for the one frame, based on an error between a target duty ratio of the pulsed light and an actual duty ratio limited by the first temporal resolution.

Example 10. An endoscope system comprising:

an endoscope including an insertion portion in which an image pickup device is incorporated, the image pickup device having a plurality of pixels that receive light from an object, to generate pixel signals, the object being illuminated with pulsed light for a plurality of times in one frame; and a light source apparatus, wherein the light source apparatus includes a processor that controls a light source configured to generate the pulsed light with which the object is illuminated and causes the light source to generate the pulsed light with a first temporal resolution, and the processor is configured to:

calculate, based on a vibration frequency of the object, a light emission cycle of the pulsed light with a second temporal resolution which is more precise than the first temporal resolution;

round the light emission cycle calculated with the second temporal resolution to a precision of the first temporal resolution, to set the light emission cycle obtained by the rounding as the light emission cycle of the pulsed light that is generated by the light source;

accumulate an error between the light emission cycle calculated with the second temporal resolution and the light emission cycle with the first temporal resolution that is obtained by the rounding;

increase the light emission cycle with the first temporal resolution in a unit of the first temporal resolution and decrease the accumulated error in the unit of the first temporal resolution, when the accumulated error reaches a predetermined positive value; and decrease the light emission cycle with the first temporal resolution in the unit of the first temporal resolution and increase the accumulated error in the unit of the first temporal resolution, when the accumulated error reaches a predetermined negative value.

What is claimed is:

1. A light source apparatus comprising:

at least one processor comprising hardware, the at least one processor being configured to:

determine, in a first unit, a first frequency of a pulsed light with a first resolution and a second frequency of pulsed light with a second resolution based on a vibration frequency of an object, the first resolution being more precise than the second resolution;

determine a difference between the first frequency and the second frequency in the first unit;

determine accumulated differences including the difference in the first unit; and when the accumulated differences reach a first predetermined value, add a second predetermined value to the second frequency in a second unit subsequent to the first unit, and subtract a third predetermined value from the accumulated differences in the second unit.

2. The light source apparatus according to claim 1, wherein the first unit is a period of a horizontal line of an image sensor, an image having a plurality of a horizontal lines including pixels, the horizontal line is obtained under the pulsed light for a plurality of times.

3. The light source apparatus according to claim 2, wherein the determining of the second resolution is obtained by rounding the first resolution, the rounding including rounding off, rounding up, or rounding down a digit after a decimal point of the first resolution, and the second resolution is set to a unit of the period of the horizontal line.

4. The light source apparatus according to claim 1, wherein the first predetermined value is 0.5 or −0.5.

5. The light source apparatus according to claim 1, wherein the processor is configured to:

perform Fourier transformation processing on a signal of the vibration frequency of the object to obtain a first fundamental frequency of the vibration;

cut the first fundamental frequency from the signal to obtain a second fundamental frequency being more precise than the first fundamental frequency.

6. The light source apparatus according to claim 5, wherein the processor is configured to:

determine validity of a frequency interval of respective peaks obtained by the Fourier transformation processing; and determine the fundamental frequency based on the determined validity.

7. A light source apparatus comprising:

at least one processor comprising hardware, the at least one processor being configured to:

control a light source that generates pulsed light with which an object is illuminated, and cause the light source to generate the pulsed light with a first temporal resolution, calculate, based on a vibration frequency of the object, a light emission cycle of the pulsed light with a second temporal resolution which is more precise than the first temporal resolution;

round the light emission cycle calculated with the second temporal resolution to a precision of the first temporal resolution, to set the light emission cycle obtained by the rounding as the light emission cycle of the pulsed light that is generated by the light source;

accumulate an error between the light emission cycle calculated with the second temporal resolution and the light emission cycle with the first temporal resolution calculated by the rounding;

increase the light emission cycle with the first temporal resolution in a unit of the first temporal resolution and decrease the accumulated error in the unit of the first temporal resolution, when the accumulated error reaches a predetermined positive value; and decrease the light emission cycle with the first temporal resolution in the unit of the first temporal resolution and increase the accumulated error in the unit of the first temporal resolution, when the accumulated error reaches a predetermined negative value.

8. The light source apparatus according to claim 7, wherein the first temporal resolution is a single horizontal line period of an image pickup device having a plurality of pixels that receive light from the object, to generate pixel signals, the object being illuminated with the pulsed light for a plurality of times in one frame.

9. The light source apparatus according to claim 8, wherein the rounding by the at least one processor is to one of round off, round up, or round down a digit after a decimal point, to thereby set the light emission cycle of the pulsed light that is generated by the light source to a unit of the single horizontal line period.

10. The light source apparatus according to claim 8, wherein the at least one processor is configured to: increase the cycle of the pulsed light that is generated by the light source by the single horizontal line period when the accumulated error becomes 0.5 or more, and decrease the cycle of the pulsed light that is generated by the light source by the single horizontal line period when the accumulated error becomes −0.5 or less.

11. The light source apparatus according to claim 7, wherein the at least one processor is configured to:

perform Fourier transformation processing on a signal based on a vibration of the object with a first precision, to obtain a fundamental frequency of the vibration;

perform filter processing, with the fundamental frequency of the vibration obtained by the Fourier transformation processing as a cut frequency, on the signal based on the vibration of the object; and obtain, based on the signal after the filter processing, the fundamental frequency of the vibration with a second precision higher than the first precision.

12. The light source apparatus according to claim 11, wherein the at least one processor is configured to determine the fundamental frequency based on a determination result of validity of a frequency interval of respective peaks obtained by the Fourier transformation processing performed with the first precision.

13. A light source apparatus for use with an endoscope, the light source apparatus comprising:

a light source; and the at least one processor according to claim 7, wherein the at least one processor is further configured to:

control the light source that generates the pulsed light so as to round the light emission cycle calculated with the second temporal resolution to a precision of the first temporal resolution and to set the light emission cycle obtained by the rounding as the light emission cycle of the pulsed light;

receive, from the image pickup device, first pixel signals and second pixel signals, the first pixel signals being pixel signals for one frame read at a readout timing, at least a part of which includes an illumination period of the pulsed light, the second pixel signals being pixel signals for one frame read at a readout timing that is one frame after the readout timing of the first pixel signals, in an overlap line in which the illumination period of the pulsed light and the readout timing overlap with each other of the plurality of pixels, synthesize a pixel signal, which corresponds to the overlap line, among the first pixel signals and a pixel signal, which corresponds to the overlap line, among the second pixel signals, to generate pixel signals for one frame; and perform one of (i) first gain correction on the synthesized pixel signals for the one frame, or (ii) multiply the synthesized pixel signals for the one frame by a gain proportional to a number of multiple exposures with the pulsed light that occur during the one frame.

14. A light source apparatus for use with an endoscope, the light source apparatus comprising:

a light source; and the at least one processor according to claim 7, wherein the at least one processor is further configured to:

control the light source that generates the pulsed light so as to round the light emission cycle calculated with the second temporal resolution to a precision of the first temporal resolution and to set the light emission cycle obtained by the rounding as the light emission cycle of the pulsed light;

receive, from the image pickup device, first pixel signals and second pixel signals, the first pixel signals being pixel signals for one frame read at a readout timing, at least a part of which includes an illumination period of the pulsed light, the second pixel signals being pixel signals for one frame read at a readout timing that is one frame after the readout timing of the first pixel signals, in an overlap line in which the illumination period of the pulsed light and the readout timing overlap with each other of the plurality of pixels, synthesize a pixel signal, which corresponds to the overlap line, among the first pixel signals and a pixel signal, which corresponds to the overlap line, among the second pixel signals, to generate pixel signals for one frame; and perform one of (i) first gain correction on the synthesized pixel signals for the one frame, or (ii) second gain correction on the synthesized pixel signals for the one frame, based on an error between a target duty ratio of the pulsed light and an actual duty ratio limited by the first temporal resolution, wherein the first temporal resolution is a single horizontal line period of the image pickup device having a plurality of pixels that receive light from the object, to generate pixel signals, the object being illuminated with the pulsed light for a plurality of times in one frame.

15. An endoscope system comprising:

an endoscope including an insertion portion having an image pickup device, the image pickup device having a plurality of pixels that receive light from an object, and generate pixel signals, the object being illuminated with pulsed light for a plurality of times in one frame; and a light source configured to generate the pulsed light with which the object is illuminated and causes the light source to generate the pulsed light with a first temporal resolution, and the at least one processor according to claim 7.

\*   \*   \*   \*   \*